United States Patent [19]

Shimazaki et al.

[11] Patent Number: 6,117,875
[45] Date of Patent: Sep. 12, 2000

[54] PYRIDO (2,3-B) PYRAZINE DERIVATIVES

[75] Inventors: Norihiko Shimazaki, Tsuchiura; Akihiko Sawada; Shinya Watanabe, both of Tsukuba, all of Japan

[73] Assignee: Fujisawa Pharmaceutical Co., Ltd., Osaka, Japan

[21] Appl. No.: 09/091,361

[22] PCT Filed: Dec. 13, 1996

[86] PCT No.: PCT/JP96/03666

§ 371 Date: Jun. 19, 1998

§ 102(e) Date: Jun. 19, 1998

[87] PCT Pub. No.: WO97/24355

PCT Pub. Date: Jul. 10, 1997

[30] Foreign Application Priority Data

Dec. 27, 1995 [GB] United Kingdom ............ 9526558

[51] Int. Cl.[7] ................ A01N 43/60; A61K 31/495; C07D 241/36
[52] U.S. Cl. .................... 514/255.01; 544/354
[58] Field of Search .................. 544/354, 255.01

[56] References Cited

U.S. PATENT DOCUMENTS 4,296,114  10/1981  Appleton et al. ............. 514/232.5

FOREIGN PATENT DOCUMENTS

96/01825  1/1996  WIPO.

*Primary Examiner*—Mukund J. Shah
*Assistant Examiner*—Tamithom N. Truong
*Attorney, Agent, or Firm*—Oblon, Spivak, McClelland, Maier & Neustadt, P.C.

[57] ABSTRACT

A compound of the formula:

wherein
$R^1$ is pyridyl(lower)alkyl, N-oxidopyridyl(lower)alkyl or imidazolyl(lower)alkyl,
$R^2$ is aminophenyl, [protected amino]phenyl, [[[halophenyl](lower)alkenoyl]amino]phenyl, [[pyridyl(lower)alkenoyl]amino]phenyl, [[[N-oxidopyridyl](lower)alkenoyl]amino]phenyl, [[[protected aminopyridyl](lower)alkenoyl]amino]phenyl, [thiazolylcarbonylamino]phenyl which may have pyridyl, naphthyl having lower alkoxy and halogen, [dihalophenyl](lower)alkenyl, [N-oxidopyridyl](lower)alkenyl, [aminopyridyl](lower)alkenyl, [protected aminopyridyl](lower)alkenyl, [carboxypyridyl](lower)alkenyl, [protected carboxypyridyl](lower)alkenyl, [[pyridyl(lower)alkenyl]pyridyl](lower)alkenyl, [[carboxy(lower)alkenyl]pyridyl](lower)alkenyl, [[protected carboxy(lower)alkenyl]pyridyl](lower)alkenyl, [pyridyl(lower)alkenyl]pyridyl, lower alkylbenzothiazolyl or [halopyridylcarbonyl]amino,
with proviso that when $R^2$ is [[4-pyridyl(lower)alkenoyl]amino]phenyl, aminophenyl, [lower alkanoylamino]phenyl or [dihalophenyl](lower)alkenyl, then
$R^1$ is N-oxidopyridyl(lower)alkyl or imidazolyl(lower)alkyl,
and a pharmaceutically acceptable salt thereof, which is useful as a medicament.

9 Claims, No Drawings

PYRIDO (2,3-B) PYRAZINE DERIVATIVES

This is a 371 application of PCT/JP96/03666 filed on Dec. 13, 1996.

TECHNICAL FIELD

This invention relates to new heterobicyclic derivatives.

One object of this invention is to provide the new and useful pyridopyrazine derivatives and pharmaceutically acceptable salts thereof which possess a strong phosphodiesterase IV (PDE IV)-inhibitory activity and a strong inhibitory activity on the production of tumor necrosis factor (TNF).

Another object of this invention is to provide processes for preparation of the pyridopyrazine derivatives and salts thereof.

A further object of this invention is to provide a pharmaceutical composition comprising said pyridopyrazine derivatives or a pharmaceutically acceptable salt thereof.

Still further object of this invention is to provide a use of said pyridopyrazine derivatives or a pharmaceutically acceptable salt thereof as a medicament for prophylactic and therapeutic treatment of PDE-IV and TNF mediated diseases such as chronic inflammatory diseases, specific autoimmune diseases, sepsis-induced organ injury, and the like in human being and animals.

DISCLOSURE OF INVENTION

The object pyridopyrazine derivatives of the present invention are novel and can be represented by the following general formula (I):

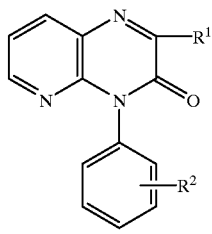

(I)

wherein
$R^1$ is pyridyl(lower)alkyl, N-oxidopyridyl(lower)alkyl or imidazolyl(lower)alkyl,
$R^2$ is aminophenyl, [protected amino]phenyl, [[[halophenyl](lower)alkenoyl]amino]phenyl, [[pyridyl(lower)alkenoyl]amino]phenyl, [[[N-oxidopyridyl](lower)alkenoyl]amino]phenyl, [[[protected aminopyridyl](lower)alkenoyl]amino]phenyl, [thiazolylcarbonylamino]phenyl which may have pyridyl, naphthyl having lower alkoxy and halogen, [dihalophenyl](lower)alkenyl, [N-oxidopyridyl](lower)alkenyl, [aminopyridyl](lower)alkenyl, [protected aminopyridyl](lower)alkenyl, [carboxypyridyl](lower)alkenyl, [protected carboxypyridyl](lower)alkenyl, [[pyridyl(lower)alkenyl]pyridyl](lower)alkenyl, [[carboxy(lower)alkenyl]pyridyl](lower)alkenyl, [[protected carboxy(lower)alkenyl]pyridyl](lower)alkenyl, [pyridyl(lower)alkenyl]pyridyl, lower alkylbenzothiazolyl or [halopyridylcarbonyl]amino,
with proviso that when $R^2$ is [[4-pyridyl(lower)alkenoyl]amino]phenyl, aminophenyl, [lower alkanoylamino]phenyl or [dihalophenyl](lower)alkenyl, then $R^1$ is N-oxidopyridyl(lower)alkyl or imidazolyl(lower)alkyl.

The object compound (I) of the present invention can be prepared by the following processes.

Process (1)

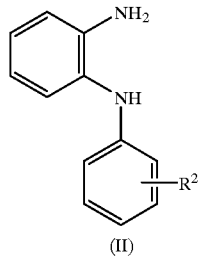

(II)
or a salt thereof

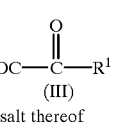

(III)
or a salt thereof

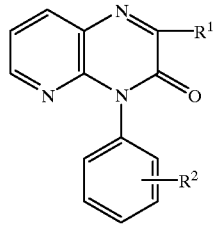

(I)
or a salt thereof

Process (2)

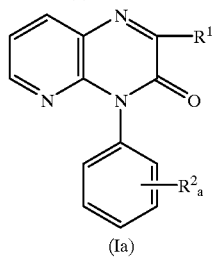

(Ia)
or its reactive derivative
at the amino group, or a salt thereof

↓ acylation

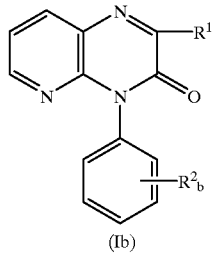

(Ib)
or a salt thereof

Process (3)

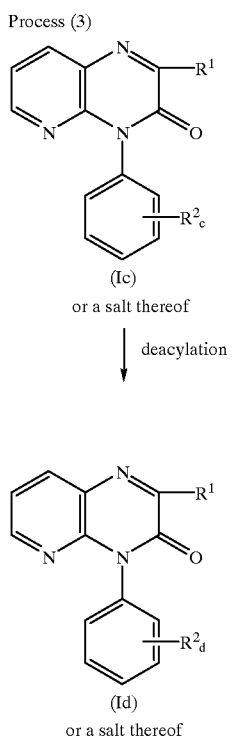

Process (4)

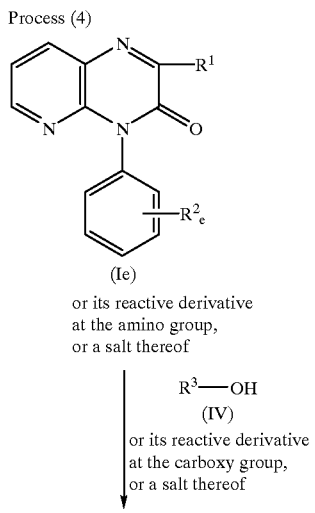

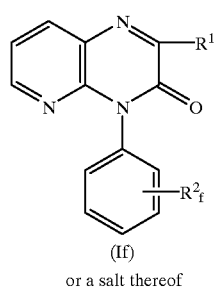

Process (5)

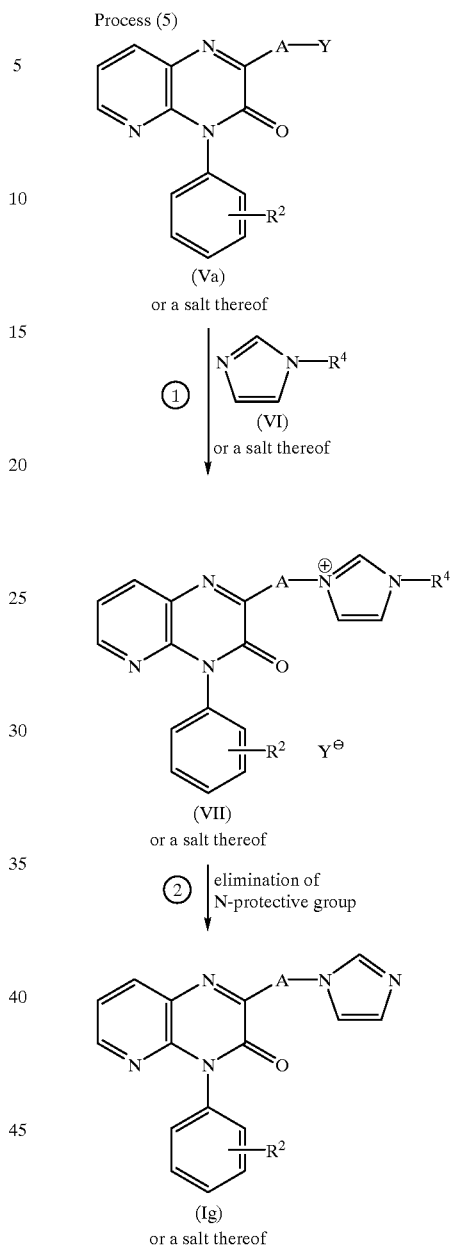

wherein
R$^1$ and R$^2$ are each as defined above,
R$_a^2$ is [aminopyridyl](lower)alkenyl,
R$_b^2$ is [acylaminopyridyl](lower)alkenyl,
R$_c^2$ is [lower alkanoylamino]phenyl, [[[halophenyl](lower)alkenoyl]amino]phenyl, [[pyridyl(lower)alkenoyl]amino]phenyl, [[[N-oxidopyridyl](lower)alkenoyl]amino]phenyl, [[[protected aminopyridyl](lower)alkenoyl]amino]phenyl, [thiazolylcarbonylamino]phenyl which may have pyridyl or [acylaminopyridyl](lower)alkenyl,
R$_d^2$ is aminophenyl or [aminopyridyl](lower)alkenyl,
R$_e^2$ is aminophenyl,
R$_f^2$ is [lower alkanoylamino]phenyl, [[[halophenyl](lower)alkenoyl]amino]phenyl, [[pyridyl(lower)alkenoyl]amino]phenyl, [[[N-oxidopyridyl](lower)alkenoyl]amino]phenyl, [[[protected aminopyridyl](lower)alkenoyl]

amino]phenyl or [thiazolylcarbonylamino]phenyl which may have pyridyl, $R^3$ is lower alkanoyl, [halophenyl](lower)alkenoyl, pyridyl (lower)alkenoyl, [N-oxidopyridyl](lower)alkenoyl, [protected aminopyridyl](lower)alkenoyl or thiazoylcarbonyl which may have pyridyl, $R^4$ is N-protective group, Y is halogen, $Y^-$ is halide, and A is lower alkylene.

The starting compound (II) of the present invention can be prepared by the following processes.

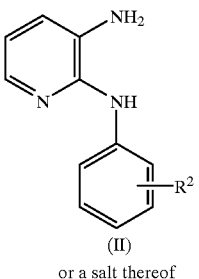

(II)
or a salt thereof

Process (A)

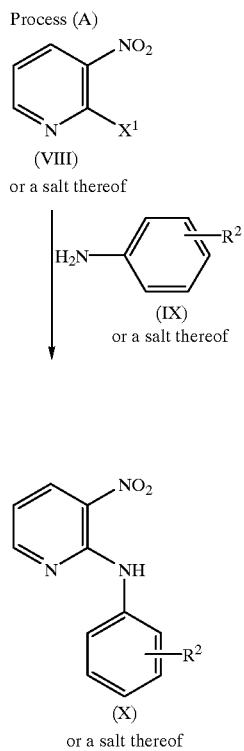

Process (C)

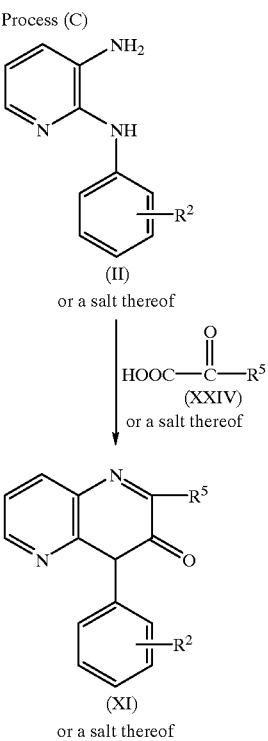

Process (B)

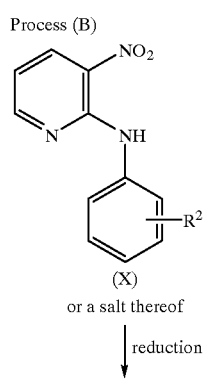

Process (D)

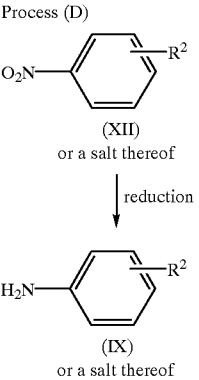

Process (E)

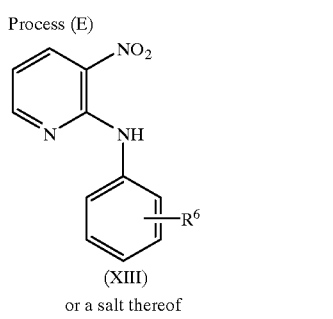

(XIII)
or a salt thereof

| elimination of
| the amino protective group
↓

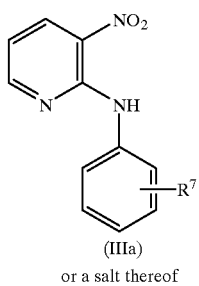

(IIIa)
or a salt thereof

Process (F)

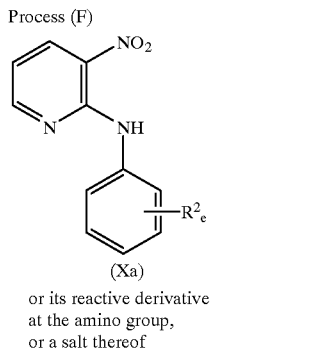

(Xa)
or its reactive derivative
at the amino group,
or a salt thereof

| $R^3$—OH
| (IV)
| or its reactive derivative
| at the carboxy group,
| or a salt thereof
↓

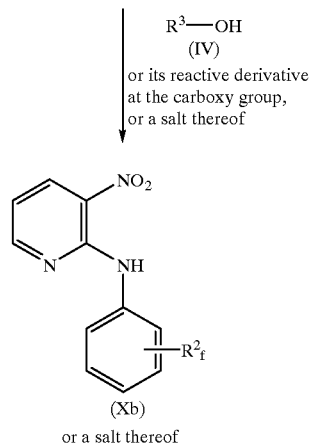

(Xb)
or a salt thereof

Process (G)

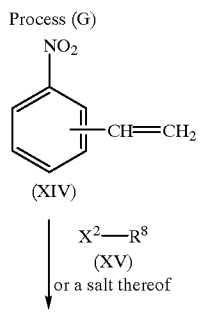

(XIV)

| $X^2$—$R^8$
| (XV)
| or a salt thereof
↓

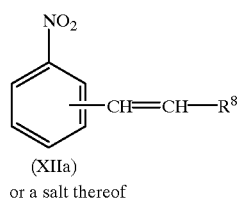

(XIIa)
or a salt thereof

Process (H)

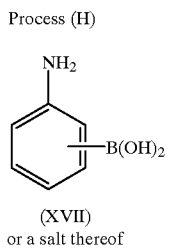

(XVII)
or a salt thereof

| $X^3$—$R^2$
| (XVIII)
| or a salt thereof
↓

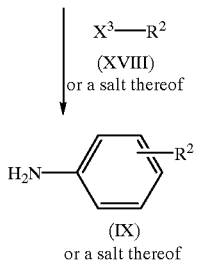

(IX)
or a salt thereof

Process (I)

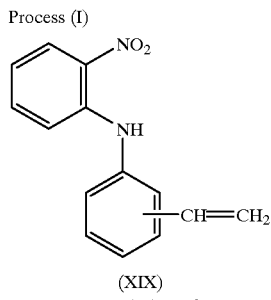

(XIX)
or a salt thereof

| $X^2$—$R^8$
| (XX)
| or a salt thereof
↓

-continued

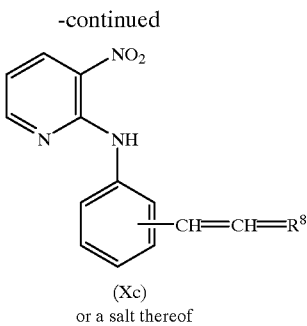

(Xc)
or a salt thereof

Process (J)

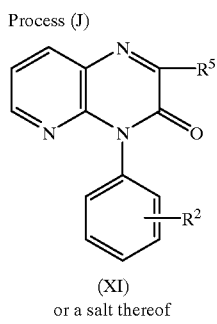

(XI)
or a salt thereof

↓ halogenation

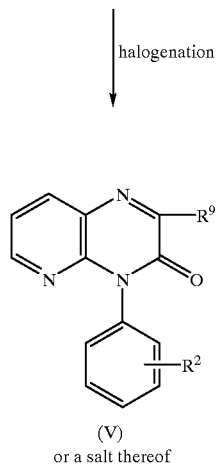

(V)
or a salt thereof

Process (K)

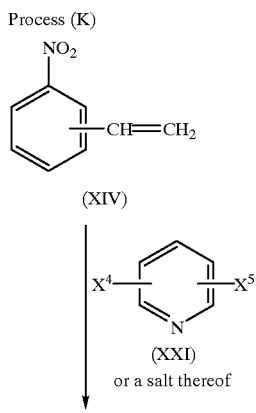

(XIV)

↓

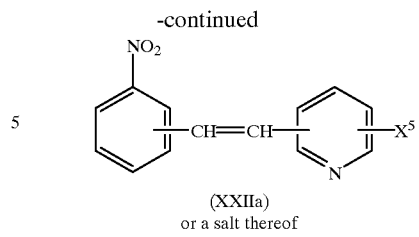

(XXI)
or a salt thereof

-continued

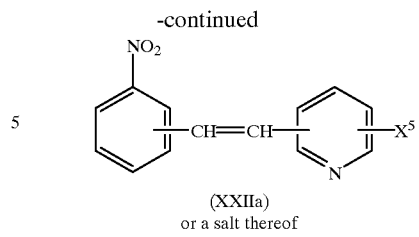

(XXIIa)
or a salt thereof

Process (L)

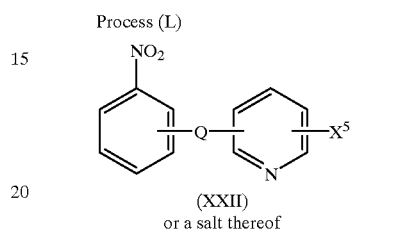

(XXII)
or a salt thereof

↓

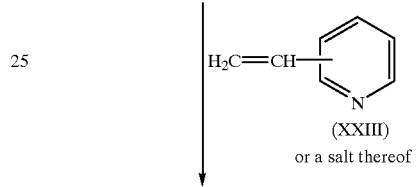

(XXIII)
or a salt thereof

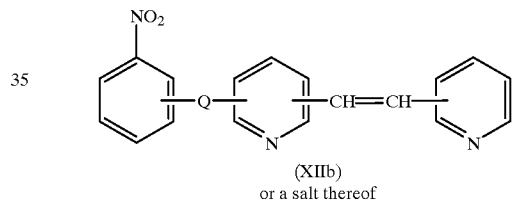

(XIIb)
or a salt thereof wherein
$R^2$, $R_e^2$, $R_f^2$ and $R^3$ are each as defined above,
$R^5$ is lower alkyl,
$R^6$ is protected aminophenyl,
$R^7$ is aminophenyl,
$R^8$ is dihalophenyl, N-oxidopyridyl, aminopyridyl, protected aminopyridyl, carboxypyridyl, protected carboxypyridyl, [pyridyl(lower)alkenyl]pyridyl, [carboxy(lower)alkenyl]pyridyl or [protected carboxy(lower)alkenyl]pyridyl,
$R^9$ is halo(lower)alkyl,
$X^1$, $X^2$, $X^3$, $X^4$ and $X^5$ are each a leaving group, and
Q is lower alkenylene.

Suitable pharmaceutically acceptable salts of the object compound (I) are conventional non-toxic salts and may include a salt with a base or an acid addition salt such as a salt with an inorganic base, for example, an alkali metal salt (e.g., sodium salt, potassium salt, etc.), an alkaline earth metal salt (e.g.., calcium salt, magnesium salt, etc.), an ammonium salt; a salt with an organic base, for example, an organic amine salt (e.g., triethylamine salt, pyridine salt, picoline salt, ethanolamine salt, triethanolamine salt, dicyclohexylamine salt, N,N'-dibenzylethylenediamine salt, etc.); an inorganic acid addition salt (e.g., hydrochloride, hydrobromide, sulfate, phosphate, etc.); an organic carboxylic or sulfonic acid addition salt (e.g., formate, acetate, trifluoroacetate, maleate, tartrate, fumarate, methanesulfonate, benzenesulfonate, toluenesulfonate, etc.); a salt with a basic or acidic amino acid (e.g., arginine, aspartic acid, glutamic acid, etc.).

In the above and subsequent descriptions of the present specification, suitable examples and illustration of the various definitions which the present invention intends to include within the scope thereof are explained in detail as follows.

The term "lower" is used to intend a group having 1 to 6, preferably 1 to 4, carbon atom(s), unless otherwise provided.

The term "higher" is used to intend a group having 7 to 20 carbon atoms, unless otherwise provided.

Suitable "lower alkyl" and "lower alkyl moiety" in the terms "pyridyl(lower)alkyl", "N-oxidopyridyl(lower)alkyl", "imidazolyl(lower)alkyl", "lower alkylbenzothiazolyl" and "halo(lower)alkyl" may include straight or branched one having 1 to 6 carbon atom(s), such as methyl, ethyl, propyl, isopropyl, butyl, isobutyl, sec-butyl, tert-butyl, pentyl, tert-pentyl, hexyl, and the like, and in which more preferable example may be $C_1$–$C_4$ alkyl, and the most preferable one may be methyl.

Suitable "lower alkenyl" and "lower alkenyl moiety" in the terms "[dihalophenyl](lower)alkenyl", "[N-oxidopyridyl](lower)alkenyl", "[aminopyridyl](lower)alkenyl", "[protected aminopyridyl](lower)alkenyl", "[carboxypyridyl](lower)alkenyl", "[protected carboxypyridyl](lower)alkenyl", [[pyridyl(lower)alkenyl]pyridyl](lower)alkenyl", "[[carboxy(lower)alkenyl]pyridyl](lower)alkenyl", [[protected carboxy(lower)alkenyl]pyridyl](lower)alkenyl" and "[pyridyl(lower)alkenyl]pyridyl" may include vinyl, 1- (or 2-)propenyl, 1-(or 2- or 3-)butenyl, 1-(or 2- or 3- or 4-)pentenyl, 1-(or 2- or 3- or 4- or 5-)hexenyl, methylvinyl, ethylvinyl, 1-(or 2- or 3-)methyl-1-(or 2-)propenyl, 1-(or 2- or 3-)ethyl-1-(or 2-)propenyl, 1-(or 2- or 3- or 4-)methyl-1-(or 2- or 3-)butenyl, and the like, in which more preferable example may be $C_2$–$C_4$ alkenyl, and the most preferable one may be vinyl.

Suitable "lower alkynyl" may include ethynyl, 1-propynyl, propargyl, 1-methylpropargyl, 1 or 2 or 3-butynyl, 1 or 2 or 3 or 4-pentynyl, 1 or 2 or 3 or 4 or 5-hexynyl, and the like.

Suitable "lower alkoxy" may include methoxy, ethoxy, propoxy, isopropoxy, butoxy, isobutoxy, t-butoxy, pentyloxy, t-pentyloxy, hexyloxy and the like.

Suitable "lower alkylene" may include straight or branched one such as methylene, ethylene, trimethylene, tetramethylene, pentamethylene, hexamethylene, methylmethylene, ethylethylene, propylene, and the like, in which more preferable example may be $C_1$–$C_4$ alkylene and the most preferable one may be methylene.

Suitable "lower alkenylene" may include straight or branched one having 2 to 6 carbon atom(s) such as vinylene, propenylene, 1-(or 2-)butenylene, 1-(or 2- or 3-)pentenylene, 1-(or 2- or 3-)hexenylene, methylvinylene, ethylvinylene, 1-(or 2- or 3-)methylpropenylene, 1-(or 2- or 3-)ethylpropenylene, 1-(or 2- or 3- or 4-)methyl-1-(or 2-)butenylene, and the like.

Suitable "cyclo(lower)alkyl" may include cyclopentyl, cyclohexyl and the like.

Suitable "cyclo(lower)alkenyl" may include cyclohexenyl, cyclohexadienyl and the like.

Suitable "aryl" may include phenyl, naphthyl and the like.

Suitable "halogen" and "halogen moiety" in the terms "halo(lower)alkyl", [[[halophenyl](lower)alkenoyl]amino] phenyl", "[dihalophenyl](lower)alkenyl" and "[halopyridylcarbonyl]amino" may include fluorine, bromine, chlorine and iodine.

Suitable "leaving group" may include acid residue, lower alkoxy as exemplified above, and the like.

Suitable "acid residue" may include halogen as exemplified above, acyloxy and the like.

Suitable "halide" may include fluoride, bromide, chloride and the like.

Suitable "protected carboxy" and "protected carboxy moiety" in the terms "[protected carboxypyridyl](lower)alkenyl and [[protected carboxy(lower)alkenyl]pyridyl](lower)alkenyl" may include esterified carboxy and the like. And suitable example of said ester may be the ones such as lower alkyl ester (e.g., methyl ester, ethyl ester, propyl ester, isopropyl ester, butyl ester, isobutyl ester, t-butyl ester, pentyl ester, t-pentyl ester, hexyl ester, etc.); lower alkenyl ester (e.g., vinyl ester, allyl ester, etc.); lower alkynyl ester (e.g. ethynyl ester, propynyl ester, etc.); lower alkoxy(lower) alkyl ester (e.g., methoxymethyl ester, ethoxymethyl ester, isopropoxymethyl ester, 1-methoxyethyl ester, 1-ethoxyethyl ester, etc.); lower alkylthio(lower)alkyl ester (e.g., methylthiomethyl ester, ethylthiomethyl ester, ethylthioethyl ester, isopropoxythiomethyl ester, etc.); mono(or di or tri)halo(lower)alkyl ester (e.g., 2-iodoethyl ester, 2,2,2-trichloroethyl ester, etc.); lower alkanoyloxy(lower)alkyl ester (e.g., acetoxymethyl ester, propionyloxymethyl ester, butyryloxymethyl ester, valeryloxymethyl ester, pivaloyloxymethyl ester, hexanoyloxymethyl ester, 1-acetoxyethyl ester, 2-acetoxyethyl ester, 2-propionyloxyethyl ester, etc.); lower alkoxycarbonyloxy(lower)alkyl ester (e.g., methoxycarbonyloxymethyl ester, ethoxycarbonyloxymethyl ester, propoxycarbonyloxymethyl ester, 1-(or 2-)[methoxycarbonyloxy]ethyl ester, 1-(or 2-)[ethoxycarbonyloxy]ethyl ester, 1-(or 2-)[propoxycarbonyloxy]ethyl ester, 1-(or 2-)[isopropoxycarbonyloxy]ethyl ester, etc.); lower alkanesulfonyl(lower)alkyl ester (e.g., mesylmethyl ester, 2-mesylethyl ester, etc.); lower alkoxycarbonyloxy(lower) alkyl ester (e.g., methoxycarbonyloxymethyl ester, ethoxycarbonyloxymethyl ester, propoxycarbonyloxymethyl ester, t-butoxycarbonyloxymethyl ester, 1-(or 2-)methoxycarbonyloxyethyl ester, 1-(or 2-)ethoxycarbonyloxyethyl ester, 1-(or 2-)isopropoxycarbonyloxyethyl ester, etc.); phthalidylidene (lower)alkyl ester; (5-lower alkyl-2-oxo-1,3-dioxol-4-yl) (lower)alkyl ester [e.g., (5-methyl-2-oxo-1,3-dioxol-4-yl) methyl ester, (5-ethyl-2-oxo-1,3-dioxol-4-yl)methyl ester, (5-propyl-2-oxo-1,3-dioxol-4-yl)ethyl ester, etc.]; mono(or di or tri)alkyl(lower)alkyl ester, for example, mono(or di or tri)phenyl(lower)alkyl ester which may have one or more suitable substituent(s) (e.g., benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-t-butylbenzyl ester, etc.); aryl ester which may have one or more suitable substituent(s) such as substituted or unsubstituted phenyl ester (e.g., phenyl ester, tolyl ester, t-butylphenyl ester, xylyl ester, mesityl ester, cumenyl ester, 4-chlorophenyl ester, 4-methoxyphenyl ester, etc.); tri(lower)alkylsilyl ester; lower alkylthioester (e.g. methylthioester, ethylthioester, etc.) and the like, in which more preferable example may be $C_1$–$C_4$ alkoxycarbonyl and the most preferable one may be methoxycarbonyl.

Suitable "hydroxy protective group" in the term "protected hydroxy" may include acyl, mono(or di or tri)phenyl (lower)alkyl which may have one or more suitable substituent(s) (e.g., benzyl, 4-methoxybenzyl, trityl, etc.), trisubstituted silyl [e.g., tri(lower)alkylsilyl (e.g., trimethylsilyl, t-butyldimethylsilyl, etc.), etc.], tetrahydropyranyl and the like.

Suitable "N-protective group" may include acyl or a conventional protecting group such as mono (or di or tri)aryl(lower)alkyl, for example, mono(or di or tri)phenyl (lower)alkyl (e.g., benzyl, trityl, etc.) or the like.

Suitable "protected amino" and "protected amino moiety" in the terms "[protected amino]phenyl", "[[[protected aminopyridyl](lower)alkenoyl]amino]phenyl" and "[protected aminopyridyl](lower)alkenyl]" may include acylamino or an amino group substituted by a conventional protecting group such as mono (or di or tri)aryl(lower)alkyl, for example, mono(or di or tri)phenyl(lower)alkyl (e.g., benzyl, trityl, etc.) or the like.

Suitable "acyl" and "acyl moiety" in the terms "acylamino" and "acyloxy" may include carbamoyl, thiocarbamoyl, aliphatic acyl group and acyl group containing an aromatic ring, which is referred to as aromatic acyl, or heterocyclic ring, which is referred to as heterocyclic acyl.

Suitable example of said acyl may be illustrated as follows:

Carbamoyl; Thiocarbamoyl;

Aliphatic acyl such as lower or higher alkanoyl (e.g., formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, icosanoyl, etc.);

lower or higher alkenoyl (e.g., acryloyl, 2-(or 3-)butenoyl, 2-(or 3- or 4-)pentenoyl, 2-(or 3- or 4- or 5-)hexenoyl, etc.);

lower or higher alkoxycarbonyl (e.g., methoxycarbonyl, ethoxycarbonyl, isopropoxycarbonyl, t-butoxycarbonyl, t-pentyloxycarbonyl, heptyloxycarbonyl, etc.);

lower or higher alkylsulfonyl (e.g., methylsulfonyl, ethylsulfonyl, etc.);

lower or higher alkoxysulfonyl (e.g., methoxysulfonyl, ethoxysulfonyl, etc.);

lower alkadienoyl (e.g., heptadienoyl, hexadienoyl, etc.);

cyclo(lower)alkylcarbonyl (e.g., cyclopropylcarbonyl, cyclopentylcarbonyl, cyclohexylcarbonyl, etc.);

cyclo(lower)alkylidene(lower)alkanoyl (e.g., cycloheptylideneacetyl, cycloheptylidenepropanoyl, cyclohexylideneacetyl, cyclohexylidenepropanoyl, etc.);

cyclo(lower)alkyloxycarbonyl (e.g., cyclopentyloxycarbonyl, cyclohexyloxycarbonyl, etc.);

lower alkylglyoxyloyl (e.g., methylglyoxyloyl, ethylglyoxyloyl, propylglyoxyloyl, etc.);

lower alkoxyglyoxyloyl (e.g., methoxyglyoxyloyl, ethoxyglyoxyloyl, propoxyglyoxyloyl, etc.);

or the like;

Aromatic acyl such as aroyl (e.g., benzoyl, toluoyl, naphthoyl, etc.);

ar(lower)alkanoyl [e.g., phenyl(lower)alkanoyl (e.g., phenylacetyl, phenylpropanoyl, phenylbutanoyl, phenylisobutanoyl, phenylpentanoyl, phenylhexanoyl, etc.), naphthyl(lower)alkanoyl (e.g., naphthylacetyl, naphthylpropanoyl, naphthylbutanoyl, etc.), etc.];

ar(lower)alkenoyl [e.g., phenyl(lower)alkenoyl (e.g., phenylpropenoyl, phenylbutenoyl, phenylmethacryloyl, phenylpentenoyl, phenylhexenoyl, etc.), naphthyl(lower) alkenoyl (e.g., naphthylpropenoyl, naphthylbutenoyl, etc.), etc.];

ar(lower)alkoxycarbonyl [e.g., phenyl(lower)alkoxycarbonyl (e.g., benzyloxycarbonyl, etc.), etc.];

aryloxycarbonyl (e.g., phenoxycarbonyl, naphthyloxycarbonyl, etc.);

aryloxy(lower)alkanoyl (e.g., phenoxyacetyl, phenoxypropionyl, etc.);

arylglyoxyloyl (e.g., phenylglyoxyloyl, naphthylglyoxyloyl, etc.);

arylsulfonyl (e.g., phenylsulfonyl, p-tolylsulfonyl, etc.);

ar(lower)alkylsulfonyl [e.g., phenyl(lower)alkylsulfonyl (e.g., benzylsulfonyl, phenylethylsulfonyl, etc.), naphthyl (lower)alkylsulfonyl (e.g., naphthylmethylsulfonyl, naphthylethylsulfonyl, etc.), etc.]; or the like;

Heterocyclic acyl such as heterocycliccarbonyl;

heterocyclic(lower)alkanoyl (e.g., heterocyclicacetyl, heterocyclicpropanoyl, heterocyclicbutanoyl, heterocyclicpentanoyl, heterocyclichexanoyl, etc.);

heterocyclic(lower)alkenoyl (e.g., heterocyclicpropenoyl, heterocyclicbutenoyl, heterocyclicpentenoyl, heterocyclichexenoyl, etc.); heterocyclicglyoxyloyl;

heterocyclicoxycarbonyl; or the like;

in which suitable "heterocyclic moiety" in the terms "heterocycliccarbonyl", "heterocyclic(lower)alkanoyl", heterocyclic(lower)alkenoyl", heterocyclicoxycarbonyl and "heterocyclicglyoxyloyl" as mentioned above means, in more detail, saturated or unsaturated, monocyclic or polycyclic heterocyclic group containing at least one hetero-atom such as an oxygen, sulfur, nitrogen atom and the like.

And, especially preferable heterocyclic group may be heterocyclic group such as unsaturated 3 to 8-membered (more preferably 5 or 6-membered) heteromonocyclic group containing 1 to 4 nitrogen atom(s), for example, pyrrolyl, pyrrolinyl, imidazolyl, pyrazolyl, pyridyl, dihydropyridyl, pyrimidinyl, pyrazinyl, pyridazinyl, triazolyl (e.g., 1H-1,2,4-triazolyl, 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), etc.;

saturated 3 to 8-membered (more preferably 5 or 6-membered) heteromonocyclic group containing 1 to 4 nitrogen atom(s), for example, pyrrolidinyl, imidazolidinyl, piperidyl, piperazinyl, etc.;

unsaturated condensed heterocyclic group containing 1 to 4 nitrogen atom(s), for example, indolyl, isoindolyl, indolinyl, indolizinyl, benzimidazolyl, quinolyl, tetrahydroquinolyl (e.g., 1,2,3,4-tetrahydroquinolyl, etc.), isoquinolyl, indazolyl, benzotriazolyl, benzopyrimidinyl (e.g., benzo[b] pyrimidinyl, etc.), etc.;

unsaturated 3 to 8-membered (more preferably 5 or 6-membered) heteromonocyclic group containing 1 to 2 oxygen atom(s) and 1 to 3 nitrogen atom(s), for example, oxazolyl, isoxazolyl, oxadiazolyl (e.g., 1,2,4-oxadiazolyl, 1,3,4-oxadiazolyl, 1,2,5-oxadiazolyl, etc.), etc.;

saturated 3 to 8-membered (more preferably 5 or 6-membered) heteromonocyclic group containing 1 to 2 oxygen atom(s) and 1 to 3 nitrogen atom(s), for example, morpholinyl, sydnonyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered (more preferably 5 or 6-membered) heteromonocyclic group containing 1 to 2 sulfur atom(s) and 1 to 3 nitrogen atom(s), for example, thiazolyl, isothiazolyl, thiadiazolyl (e.g., 1,2,3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered (more preferably 5 or 6-membered) heteromonocyclic group containing 1 to 2 sulfur atom(s) and 1 to 3 nitrogen atom(s), for example, thiazolidinyl, etc.;

unsaturated 3 to 8-membered (more preferably 5 or 6-membered) heteromonocyclic group containing 1 to 2 sulfur atom(s), for example, thienyl, dihydrodithiinyl, dihydrodithionyl, etc.;

unsaturated condensed heterocyclic group containing 1 to 2 sulfur atom(s) and 1 to 3 nitrogen atom(s), for example, benzothiazolyl, benzothiadiazolyl, etc.;

unsaturated 3 to 8-membered (more preferably 5 or 6-membered) heteromonocyclic group containing an oxygen atom, for example, furyl, etc.;

unsaturated condensed heterocyclic group containing 1 to 2 oxygen atom(s), for example, benzodioxolyl (e.g. methylenedioxyphenyl, etc.), benzofuryl, etc.;

unsaturated 3 to 8-membered (more preferably 5 or 6-membered) heteromonocyclic group containing an oxygen atom and 1 to 2 sulfur atom(s), for example, dihydrooxathiinyl, etc.;

unsaturated condensed heterocyclic group containing 1 to 2 sulfur atom(s), for example, benzothienyl (e.g., benzo[b]thienyl, etc.), benzodithiinyl, etc.;

unsaturated condensed heterocyclic group containing an oxygen atom and 1 to 2 sulfur atom(s), for example, benzoxathiinyl, etc.; and the like.

The acyl moiety as stated above may have one to ten, same or different, suitable substituent(s) such as lower alkyl as exemplified above, lower alkoxy as exemplified above, lower alkylthio wherein lower alkyl moiety is as exemplified above, cyclo(lower)alkyl as exemplified above, cyclo(lower)alkenyl as exemplified above, cyclo(lower)alkyloxy wherein cyclo(lower)alkyl moiety is as exemplified above, halogen as exemplified above, amino, protected amino as exemplified above, hydroxy, protected hydroxy as exemplified above, cyano, nitro, carboxy, protected carboxy as exemplified above, sulfo, sulfamoyl, imino, oxo, amino (lower)alkyl wherein lower alkyl moiety is as exemplified above, carbamoyloxy, mono(or di or tri)halo(lower)alkyl wherein halogen moiety and lower alkyl moiety are each as exemplified above, hydroxy(lower)alkyl wherein lower alkyl moiety is as exemplified above, heterocyclic group as exemplified above, heterocyclicoxy wherein heterocyclic moiety is as exemplified above, heterocyclicamino which may have nitro wherein heterocyclic moiety is as exemplified above, aryl which may have suitable substituent(s) wherein aryl moiety is as exemplified above, arylsulfonyl wherein aryl moiety is as exemplified above, ar(lower)alkyl wherein aryl moiety and lower alkyl moiety are each as exemplified above, protected carboxy(lower)alkenyl wherein protected carboxy moiety and lower alkenyl moiety are each as exemplified above, acyl as exemplified above, acylamino wherein acyl moiety is as exemplified above, or the like.

Preferable acyl thus defined may be aliphtic acyl such as lower alkanoyl (e.g. acetyl, etc.) and the most preferable one may be acetyl.

Suitable "lower alkanoyl moiety" in the term "[lower alkanoylamino]phenyl" can be referred to the ones as mentioned above.

Suitable "lower alkenoyl moiety" in the terms "[[[halophenyl](lower)alkenoyl]amino]phenyl", "[[pyridyl(lower)alkenoyl]amino]phenyl", [[[(N-oxidopyridyl](lower)alkenoyl]amino]phenyl" and "[[[protected aminopyridyl](lower)alkenoyl]amino]phenyl" can be referred to the ones as mentioned above.

The processes for preparing the object and the starting compounds are explained in detail in the following.

Process (1)

The compound (I) or a salt thereof can be prepared by reacting the compound (II) or a salt thereof with the compound (III) or a salt thereof.

This reaction is usually carried out in a solvent such as water, alcohol (e.g., methanol, ethanol, etc.), benzene, N,N-dimethylformamide, tetrahydrofuran, toluene, methylene chloride, ethylene dichloride, chloroform, diethyl ether or any other solvent which does not adversely affect the reaction.

The reaction temperature is not critical and the reaction is usually carried out under warming to heating.

Process (2)

The compound (Ib) or a salt thereof can be prepared by subjecting the compound (Ia) or its reactive derivative at the amino group or a salt thereof to acylation reaction.

Suitable acylating agent to be used in the present acylation reaction may include the compound of the formula:

$R^{11}$—OH　　　　　　　　　　　　　　　　(XXV)

(wherein $R^{11}$ is acyl)

or its reactive derivative or a salt thereof.

Suitable reactive derivative at the amino group of the compound (Ia) may include Schiff's base type imino or its tautomeric enamine type isomer formed by the reaction of the compound (Ia) with a carbonyl compound such as aldehyde, ketone or the like; a silyl derivative formed by the reaction of the compound (Ia) with a silyl compound such as N,O-bis(trimethylsilyl)acetamide, N-trimethylsilylacetamide or the like; a derivative formed by the reaction of the compound (Ia) with phosphorus trichloride or phosgene, and the like.

Suitable reactive derivative of the compound (XXV) may include an acid halide, an acid anhydride, an activated ester, isocyanate, and the like. The suitable example may be an acid chloride; acid azide; a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, alkanesulfuric acid (e.g., methanesulfonic acid, ethanesulfonic acid, etc.), sulfuric acid, alkylcarbonic acid, aliphatic carboxylic acid (e.g, pivalic acid, pentanoic acid, isopentanoic acid, 2-ethylbutyric acid, trichloroacetic acid, etc.); aromatic carboxylic acid (e.g., benzoic acid, etc.); a symmetrical acid anhydride; an activated amide with imidazole, 4-substituted imidazole, dimethylpyrazole, triazole or tetrazole; an activated ester (e.g., cyanomethyl ester, methoxymethyl ester, dimethyliminomethyl [$(CH_3)_2{}^+$N=CH—] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenylthio ester, p-nitrophenyl thioester, p-cresyl thioester, carboxymethyl thioester, pyranyl ester, pyridyl ester, piperidyl ester, 8-quinolyl thioester, etc.); an ester with a N-hydroxy compound (e.g., N,N-dimethylhydroxylamine, 1-hydroxy-2-(1H)-pyridone, N-hydroxysuccinimide, N-hydroxybenzotriazole, N-hydroxyphthalimide, 1-hydroxy-6-chloro-1H-benzotriazole, etc.); substituted or unsubstituted aryl isocyanate; substituted or unsubstituted aryl isothiocyanate, and the like. These reactive derivatives can optionally be selected from them accordingly to the kind of the compound (XXV) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvents which do not adversely influence the reaction. These conventional solvents may also be used in a mixture with water.

When the compound (XXV) is used in free acid form or its salt form in the reaction, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diisopropylcarbodiimide; N-ethyl-N'-(3-dimethylaminopropyl)carbodiimide; N,N-carbonyl-bis(2-methylimidazole); pentamethyleneketene-N-cyclohexylimine; diphenylketene-N-cyclohexylimine; ethoxyacetylene; 1-alkoxy-1-chloroethylene; trialkyl phosphite; isopropyl polyphosphate; phosphorous oxychloride (phosphoryl chloride); phosphorous trichloride; thionyl chloride; oxalyl chloride; triphenylphosphite; 2-ethyl-7-hydroxybenzisoxazolium salt; 2-ethyl-5-(m-sulfophenyl) isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, phosphorous oxychloride, etc.; or the like.

The reaction may also be carried out in the presence of an organic or inorganic base such as an alkali metal bicarbonate, tri(lower)alkylamine, pyridine, N-(lower) alkylmorphorine, N,N-di(lower)alkylbenzylamine, or the like.

The reaction temperature is not critical, and the reaction is usually carried out under cooling to heating.

Process (3)

The compound (Id) or a salt thereof can be prepared by subjecting the compound (Ic) or a salt thereof to deacylation reaction.

Suitable method of this deacylation reaction may include conventional one such as hydrolysis, reduction and the like.

(i) For Hydrolysis:

The hydrolysis is preferably carried out in the presence of a base or an acid including Lewis acid.

Suitable base may include an inorganic base and an organic base such as an alkali metal [e.g., sodium, potassium, etc.], an alkaline earth metal [e.g., magnesium, calcium, etc.], the hydroxide or carbonate or hydrogencarbonate thereof, trialkylamine [e.g., trimethylamine, triethylamine, etc.], picoline, 1,5-diazabicyclo[4.3.0]non-5-ene, or the like.

Suitable acid may include an organic acid [e.g., formic acid, acetic acid, propionic acid, trichloroacetic acid, trifluoroacetic acid, etc.], and an inorganic acid [e.g., hydrochloric acid, hydrobromic acid, sulfuric acid, hydrogen chloride, hydrogen bromide, etc.].

The elimination using Lewis acid such as trihaloacetic acid [e.g., trichloroacetic acid, trifluoroacetic acid, etc.], or the like is preferably carried out in the presence of cation trapping agents [e.g., anisole, phenol, etc.].

The reaction is usually carried out in a conventional solvent such as water, alcohol (e.g., methanol, ethanol, isopropyl, alcohol, etc.), tetrahydrofuran, dioxane, toluene, methylene chloride, ethylene dichloride, chloroform, N,N-dimethylformamide, N,N-dimethylacetamide or any other organic solvents which do not adversely affect the reaction, or the mixture thereof.

The reaction temperature is not critical and the reaction is usually carried out under cooling to warming.

(ii) For Reduction:

Reduction is carried out in a conventional manner, including chemical reduction and catalytic reduction.

Suitable reducing reagent to be used in chemical reduction are hydrides (e.g., hydrogen iodide, hydrogen sulfide, lithium aluminum hydride, sodium borohydride, sodium cyanoborohydride, etc.), or a combination of a metal (e.g., tin, zinc, iron, etc.) or metallic compound (e.g., chromium chloride, chromium acetate, etc.) and an organic acid or an inorganic acid (e.g., formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g., platinum plate, spongy platinum, platinum black, colloidal platinum, platinum oxide, platinum wire, etc.), palladium catalysts (e.g., spongy palladium, palladium black, palladium oxide, palladium on carbon, colloidal palladium, palladium on barium sulfate, palladium on barium carbonate, etc.), nickel catalysts (e.g., reduced nickel, nickel oxide, Raney nickel, etc.), cobalt catalysts (e.g., reduced cobalt, Raney cobalt, etc.), iron catalysts (e.g., reduced iron, Raney iron, Ullman iron, etc.), and the like.

The reduction is usually carried out in a conventional solvent such as water, alcohol (e.g., methanol, ethanol, isopropyl alcohol, etc.), tetrahydrofuran, dioxane, toluene, methylene chloride, ethylene dichloride, chloroform, N,N-dimethylformamide, N,N-dimethylacetamide or any other organic solvents which do not adversely affect the reaction, or the mixture thereof.

Additionally, in case that the above-mentioned acids to be used in chemical reduction are in liquid, they can also be used as a solvent.

The reaction temperature of this reduction is not critical and the reaction is usually carried out under cooling to warming.

Process (4)

The compound (If) or a salt thereof can be prepared by reacting the compound (Ie) or its reactive derivative at the amino group, or a salt thereof with the compound (IV) or its reactive drivative at the carboxy group, or a salt thereof.

This reaction can be carried out in a similar manner to that of the aforementioned Process (2), and therefore the reagents to be used and the reaction conditions (e.g., solvent, reaction temperature, etc.) can be referred to those of the Process (2).

Process (5)-1

The compound (VII) or a salt thereof can be prepared by reacting the compound (Va) or a salt thereof with the compound (VI) or a salt thereof.

This reaction is usually carried out in a solvent such as water, alcohol (e.g., methanol, ethanol, etc.), benzene, N,N-dimethylformamide, tetrahydrofuran, toluene, methylene chloride, ethylene dichloride, chloroform, dioxane, diethyl ether or any other solvents which do not adversely affect the reaction, or the mixture thereof.

The reaction temperature is not critical and the reaction is usually carried out under cooling to heating.

The reaction is usually carried out in the presence of an acid including Lewis acid.

Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid, hydrogen chloride, hydrogen bromide, zinc halide (e.g. zinc chloride, zinc bromide, etc.), etc.] and the like.

The reaction may be also carried out in the presence of an inorganic or an organic base such as an alkali metal (e.g., sodium, potassium, etc.), an alkali metal hydroxide (e.g., sodium hydroxide, potassium hydroxide, etc.), an alkali metal hydrogencarbonate (e.g., sodium hydrogencarbonate, potassium hydrogencarbonate, etc.), alkali metal carbonate (e.g., sodium carbonate, potassium carbonate, etc.), tri (lower)alkylamine (e.g., trimethylamine, triethylamine, diisopropylethylamine, etc.), alkali metal hydride (e.g., sodium hydride, etc.), alkali metal (lower)alkoxide (e.g., sodium methoxide, sodium ethoxide, etc.), pyridine, lutidine, picoline, dimethylaminopyridine, N-(lower) alkylmorpholine, N,N-di(lower)alkylbenzylamine, N,N-di (lower)alkylaniline or the like.

When the base, the acid and/or the starting compound are in liquid, they can be used also as a solvent.

Process (5)-2

The compound (Ig) or a salt thereof can be prepared by subjecting the compound (VII) or a salt thereof to elimination reaction of N-protective group.

This reaction can be carried out in a similar manner to that of the aforementioned Process (3), and therefore the reagents to be used and the reaction conditions (e.g., solvent, reaction temperature, etc.) can be referred to those of the Process (3).

Process (A)

The compound (X) or a salt thereof can be prepared by reacting the compound (VIII) or a salt thereof with the compound (IX) or a salt thereof.

This reaction is usually carried out in a solvent such as water, alcohol (e.g., methanol, ethanol, etc.), benzene, N,N-dimethylformamide, tetrahydrofuran, toluene, methylene chloride, ethylene dichloride, chloroform, diethyl ether or any other solvent which does not adversely affect the reaction.

The reaction temperature is not critical and the reaction is usually carried out under warming to heating.

When the starting compound is in liquid, it can be also used as a solvent.

Process (B)

The compound (II) or a salt thereof can be prepared by subjecting the compound (X) or a salt thereof to reduction reaction.

Reduction is carried out in a conventional manner, including chemical reduction and catalytic reduction.

Suitable reducing reagent to be used in chemical reduction are hydrides (e.g., hydrogen iodide, hydrogen sulfide, lithium aluminum hydride, sodium borohydride, sodium cyanoborohydride, etc.) or a combination of a metal (e.g., tin, zinc, iron, etc.) or metallic compound (e.g., chromium chloride, chromium acetate, etc.) and an organic acid or an inorganic acid (e.g., formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g., platinum plate, spongy platinum, platinum black, colloidal platinum, platinum oxide, platinum wire, etc.), palladium catalysts (e.g., spongy palladium, palladium black, palladium oxide, palladium on carbon, colloidal palladium, palladium on barium sulfate, palladium on barium carbonate, etc.), nickel catalysts (e.g., reduced nickel, nickel oxide, Raney nickel, etc.), cobalt catalysts (e.g., reduced cobalt, Raney cobalt, etc.), iron catalysts (e.g., reduced iron, Raney iron, etc.), copper catalysts (e.g., reduced copper, Raney copper, Ullman copper, etc.) and the like.

The reduction is usually carried out in a conventional solvent which does not adversely influence the reaction such as water, alcohol (e.g., methanol, ethanol, propanol, etc.), tetrahydrofuran, dioxane, N,N-dimethylformamide, etc., or a mixture thereof.

The reaction temperature is not critical and the reaction is usually carried out under cooling to warming.

Process (C)

The compound (XI) or a salt thereof can be prepared by reacting the compound (II) or a salt thereof with the compound (XXIV) or a salt thereof.

This reaction can be carried out in a similar manner to that of the aforementioned Process (1), and therefore the reagents to be used and the reaction conditions (e.g., solvent, reaction temperature, etc.) can be referred to those of the Process (1).

Process (D)

The compound (IX) or a salt thereof can be prepared by subjecting the compound (XII) or a salt thereof to reduction reaction.

This reaction can be carried out in a similar manner to that of the aforementioned Process (B), and therefore the reagents to be used and the reaction conditions (e.g., solvent, reaction temperature, etc.) can be referred to those of the Process (B).

Process (E)

The compound (IIa) or a salt thereof can be prepared by subjecting the compound (XIII) or a salt thereof to elimination reaction of the amino protective group.

The reaction can be carried out in the manner disclosed in Preparation 5 or 6 or similar manners thereto.

Process (F)

The compound (Xb) or a salt thereof can be prepared by reacting the compound (Xa) or its reactive derivative at the amino group, or a salt thereof with the compound (IV) or its reactive derivative at the carboxy group, or a salt thereof.

The reaction can be carried out in the manner disclosed in Preparation 16 or similar manners thereto.

Process (G)

The compound (XIIa) or a salt thereof can be prepared by reacting the compound (XIV) with the compound (XV) or a salt thereof.

The reaction can be carried out in the manner disclosed in Preparation 1 or similar manners thereto.

Process (H)

The compound (IX) or a salt thereof can be prepared by reacting the compound (XVII) or a salt thereof with the compound (XVIII) or a salt thereof.

The reaction can be carried out in the manner disclosed in Preparation 3, or similar manners thereto.

Process (I)

The compound (Xc) or a salt thereof can be prepared by reacting the compound (XIX) or a salt thereof with the compound (XX).

The reaction can be carried out in the manner disclosed in Preparation 10 or similar manners thereto.

Process (J)

The compound (V) or a salt thereof can be prepared by subjecting the compound (XI) or a salt thereof to halogenation reaction.

The reaction can be carried out in the manner disclosed in Preparation 25 or similar manners thereto.

Process (K)

The compound (XXIIa) or a salt thereof can be prepared by reacting the compound (XIV) with the compound (XXI) or a salt thereof.

The reaction can be carried out in the manner disclosed in Preparation 2 or similar manners thereto.

Process (L)

The compound (XIIb) or a salt thereof can be prepared by reacting the compound (XXII) or a salt thereof with the compound (XXIII) or a salt thereof.

The reaction can be carried out in the manner disclosed in Preparation 12 or similar manners thereto.

Suitable salts of the object and the starting compounds in Processes (1)þ(5) and (A)þ(L) can be referred to the ones as exemplified for the compound (I).

The new pyridopyrazine derivatives (I) and pharmaceutically acceptable salts thereof hardly possess a strong inhibitory activity against phosphodiesterase III (PDE III), but possess a strong inhibitory activity against phosphodiesterase IV (PDE IV) and a strong inhibitory activity on the tumor necrosis factor (TNF).

That is, the pyridopyrazine derivatives (I) and pharmaceutically acceptable salts thereof are selective inhibitors of phosphodiesterase IV (PDE IV) and inhibitors on the production of tumor necrosis factor (TNF).

Accordingly, the new pyridopyrazine derivatives (I) and a pharmaceutically acceptable salt thereof can be used for prophylactic and therapeutic treatment of PDE-IV and TNF mediated diseases such as chronic inflammatory diseases (e.g., rheumatoid arthritis, osteoarthritis, emphysema, chronic bronchiolitis, etc.), osteoporosis, rejection by transplantation, asthma, eosinophilia, cystic fibrosis, hepatitis, pancreatitis, nephritis, endotoxin shock, specific autoimmune diseases (e.g., ankylosing spondylitis, autoimmune hematological disorders (e.g., hemolyticodo anaemia, aplastic anaemia, pure red cell anaemia, idiopathic thrombocytopenia, etc.), systemic lupus erythematosus, polychondritis, scleroderma, Wegener granulamotosis, dermatomyositis, chronic active hepatitis, myasthenia gravis, atopic dermatitis, psoriasis, idiopathic sprue, autoimmune inflammatory bowel disease (e.g., ulcerative colitis, Crohn's disease, etc.), endocrine ophthalmopathy, Grave's disease, sarcoidosis, multiple sclerosis, primary biliary cirrhosis, diabetes [e.g. juvenile diabetes (diabetes mellitus type I), etc.], Reiter's syndrome, non infection uveitis, autoimmune keratitis (e.g., keratoconjunctivitis sicca, vernal keratoconjunctivitis, etc.), interstitial lung fibrosis, psoriatic arthritis, etc.], cancer cachexia, AIDS cachexia, thrombosis, and the like.

In order to show the utilities of the pyridopyrazine derivatives (I) and a pharmaceutically acceptable salt thereof of the present invention, pharmacological test data of the representative compound of the pyridopyrazine derivatives (I) are illustrated in the following.

(a) Inhibition of U937 phosphodiesterase IV (PDE IV)

1. Test Method:

Harvested U937 was freezed in −80þC. and throwed to destroy the cell body. The pellet of destroyed cell was washed by Phosphate-buffered saline (PBS).

The washed cell pellet was homogenized with Dounce homogenizer (20 strokes) in homogenizing buffer (0.5% deoxycholate [DOC], 5 mM 2-mercaptoethanol, 1 $\mu$M leupeptin, 100 $\mu$M PMSF, 20 $\mu$M p-tosyl-L-lysine-chloromethyl ketone [TLCK] in PBS). The homogenate was centrifuged at 100,000 g×90 minutes (4þC.) and the supernatant containing PDE IV activity was dialyzed against dialysis buffer, which was the same component as homogenizing buffer without DOC. The dialyzed supernatant of homogenate was stored in freezer (−80þC.) as PDE IV enzyme preparation.

Enzyme preparation was diluted in assay buffer (10 mM Tris-HCl, 5 mM MgCl, 1 mM 2-Mercaptoethanol [pH 8.0]). In advance the rate of dilution was choosen every new lot of homogenizing preparation. For blank, a part of the enzyme preparation was boiled for 10 minutes.

Test compounds were dissolved in dimethylsulfoxide (DMSO) at a concentration of 4×10(−2)[M] (final conc. 1×10(−5)M), then serial dilutions were made in DMSO to achieve desired concentrations. The diluted compounds of each concentration were further diluted 1:500 in assay buffer (0.2% DMSO). Final DMSO concentration in assay tube was 0.025%.

In duplicate, the followings were added to a glass tube, in order, at 0þC. (all concentrations are given as final concentrations in assay tube).

50 $\mu$l compound or assay buffer for control or blank

50 $\mu$l 8×10(−5)[M] CI-930 (final 10 $\mu$M): (CI-930 is PDE III inhibitor)

200 $\mu$l enzyme preparation or boiled enzyme preparation for blank.

The reaction tube was preincubated in a water bath (30p bC.) for 5 minutes, then 100 $\mu$l [$^3$H]-cAMP (37.0 MBq/ml [$^3$H]-cAMP: 4 $\mu$M cold cAMP=1:800) was added thereto. After 15 minutes, 2.5 units/ml alkaline phosphatase was added to the reaction mixture and the reaction was continued for 15 minutes. Dowex 1×8 gel was added to the reaction mixture and was vortexed well. The mixture was centrifuged at 1000 rpm×5 minutes, and then 500 $\mu$l of the supernatant was added to 10 ml scintillation fluid in appropriate vial, vortexed, and counted for [$^3$H].

The inhibitory activity was calculated according to the following equation:

$$\% \text{ Inhibition} = 100 - \frac{\text{avg. cpm[test compound]} - \text{avg. cpm[blank(boiled enzyme)]}}{\text{avg. cpm[control(no compound)]} - \text{avg. cpm[blank(boiled enzyme)]}} \times 100$$

2. Test Compound:
(a) 4-[3-[3-[(E)-3-(6-acetanido-3-pyridyl)acryloylanino]phenyl]phenyl]-2-(3-pyridylmethyl)-3-oxo-3,4-dihydropyrido[2,3-b]pyrazine.

3. Test Result:

| Test compound | IC$_{50}$ (M) |
|---|---|
| (a) | 1.6 × 10$^{-8}$ |

(b) Inhibition on TNF-α production in human mononuclear cells.

1. Test Method:

Blood was drawn from healthy volunteers with heparin. The mononuclear cell (MNC) fraction was obtained by gradient centrifugation (1800 rpm, 15 minutes), diluted with the same volume of RPMI-1640 culture medium, over Ficoll-Paque (Pharmacia LKB Biotechnology). MNC were washed twice with RPMI-1640. Then, MNC were resuspended in RPMI-1640 culture medium supplemented with 2 mM L-glutamine and 1% fetal bovine serum. MNC were incubated at 37þC. for 16 hours in 96-well micro culture plate at a concentration of 3×10$^5$ cells/well with or without 1 $\mu$g/ml lipopolysaccharide (LPS) (from *E. coli*) and various amounts of test compound. At the end of incubation, the supernatant was obtained and its TNF-α active was measured by enzyme-linked immunosorbent assay (ELISA). ELISA was performed with TNF-α ELISA kit (Otsuka Pharmaceutical Co., Ltd.).

2. Test Compound:
(a) 4-[3-[3-[(E)-3-(6-acetamido-3-pyridyl)acryloylamino]phenyl]phenyl]-2-(3-pyridylmethyl)-3-oxo-3,4-dihydropyrido[2,3-b]pyrazine.

3. Test Result:

| Test compound | IC$_{50}$ (M) |
|---|---|
| (a) | $2.4 \times 10^{-8}$ |

For therapeutic administration, the object compounds (I) of the present invention and pharmaceutically acceptable salts thereof are used in a form of the conventional pharmaceutical preparation in admixture with a conventional pharmaceutically acceptable carrier such as an organic or inorganic solid or liquid excipient which is suitable for oral, parenteral or external administration. The pharmaceutical preparation may be compounded in a solid form such as granule, capsule, tablet, dragee or suppository, or in a liquid form such as solution, suspension or emulsion for injection, ingestion, eye drops, etc. If needed, there may be included in the above preparation auxiliary substance such as stabilizing agent, wetting or emulsifying agent, buffer or any other commonly used additives.

The effective ingredient may usually be administered with a unit dose of 0.001 mg/kg to 500 mg/kg, preferably 0.01 mg/kg to 10 mg/kg, 1 to 4 times a day. However, the above dosage may be increased or decreased according to age, weight and conditions of the patient or the administering method.

Preferred embodiments of the object compound (I) are as follows.

$R^1$ is pyridyl(lower)alkyl, N-oxidopyridyl(lower)alkyl or imidazolyl(lower)alkyl, $R^2$ is aminophenyl, [lower alkanoylamino]phenyl, [[[halophenyl](lower)alkenoyl]amino]phenyl, [[pyridyl (lower)alkenoyl]amino]phenyl, [[[N-oxidopyridyl] (lower)alkenoyl]amino]phenyl, [[[acylaminopyridyl] (lower)alkenoyl]amino]phenyl (more preferably [[[[lower alkanoylamino]pyridyl](lower)alkenoyl]amino]phenyl), [[pyridylthiazolyl]carbonylamino]phenyl, naphthyl having lower alkoxy and halogen, [dihalophenyl](lower) alkenyl, [N-oxidopyridyl](lower)alkenyl, [aminopyridyl] (lower)alkenyl, [[acylamino]pyridyl](lower)alkenyl(more preferably [[lower alkanoylamino]pyridyl](lower)alkenyl or [[mono(or di or tri)halo(lower)alkanoylamino]pyridyl] (lower)alkenyl; most preferably [[lower alkanoylamino] pyridyl](lower)alkenyl or [[trihalo(lower)alkanoylamino] pyridyl](lower)alkenyl), [carboxypyridyl](lower)alkenyl, [esterified carboxypyridyl](lower)alkenyl (more preferably [lower alkoxycarbonylpyridyl](lower)alkenyl), [[pyridyl(lower)alkenyl]pyridyl](lower)alkenyl, [[carboxy(lower)alkenyl]pyridyl](lower)alkenyl, [[esterified carboxy(lower)alkenyl]pyridyl](lower) alkenyl (more preferably [[lower alkoxycarbonyl(lower) alkenyl]pyridyl](lower)alkenyl, [pyridyl(lower)alkenyl] pyridyl, lower alkylbenzothiazolyl or halopyridylcarbonylamino, with proviso that when $R^2$ is [[4-pyridyl(lower)alkenoyl] amino]phenyl, aminophenyl, [lower alkanoylamino] phenyl or [dihalophenyl](lower)alkenyl, then $R^1$ is N-oxidopyridyl(lower)alkyl or imidazolyl(lower) alkyl.

The following Preparations and Examples are given for the purpose of illustrating the present invention in more detail.

PREPARATION 1

A mixture of 3-nitrostyrene (7.0 g), 2-acetamido-5-bromopyridine (10.1 g), tetra-n-butylammonium chloride (13.1 g), palladium(II) acetate (0.08 g) and sodium bicarbonate (9.87 g) in N,N-dimethylformamide (70 ml) was stirred at 110°C. for 6 hours. The reaction mixture was poured into ice-water and precipitated crystals were collected, washed with water and dried to give 3-[(E)-2-(6-acetamido-3-pyridyl)vinyl]nitrobenzene (12.0 g).

NMR (DMSO-d$_6$, δ): 2.11 (3H, s), 7.44 (1H, d, J=16Hz), 7.50 (1H, d, J=16Hz), 7.68 (1H, dd, J=8, 8Hz), 8.04 (1H, d, J=8Hz), 8.11 (3H, m), 8.43 (1H, m or dd, J=1, 1Hz), 8.55 (1H, s, or d, J=1Hz).

PREPARATION 2

A mixture of 3-nitrostyrene (5.36 ml), 3,5-dibromopyridine (10.0 g), palladium(II) acetate (259 mg), tetra-n-butylammonium chloride (10.7 g) and sodium bicarbonate (8.07 g) in N,N-dimethylformamide (50 ml) was stirred at 120°C. for 4 hours. The mixture was poured into sodium bicarbonate solution and extracted with ethyl acetate twice. The combined organic solution was washed with sodium bicarbonate solution and brine, dried over magnesium sulfate and concentrated. The resultant solid was washed with diisopropyl ether to give 3-bromo-5-[(E)-2-(3-nitrophenyl)vinyl]pyridine (5.74 g).

NMR (CDCl$_3$, δ): 7.1–7.3 (2H, m), 7.59 (1H, t, J=8Hz), 7.82 (1H, d, J=8Hz), 8.02 (1H, t, J=2Hz), 8.18 (1H, dd, J=2, 8Hz), 8.39 (1H, t, J=2Hz), 8.11 (1H, d, J=2Hz), 8.67 (1H, d, J=2Hz).

PREPARATION 3

A mixture of 3,5-dibromopyridine (9.9 g), 3-aminophenyl-dihydroxyboraneþhemisulfate (7.77 g), tetrakis(triphenylphosphine)palladium(0) (1.06 g) and 2M aqueous sodium bicarbonate solution (42 ml) in toluene (85 ml) and methanol (21 ml) was stirred at 80°C. for 4.5 hours. The mixture was poured into sodium bicarbonate solution and extracted with ethyl acetate twice. The combined organic solution was washed with sodium bicarbonate and brine, dried over magnesium sulfate and concentrated. The residue was chromatographed on silica gel column (4% methanol in chloroform) to give 3-(3-aminophenyl)-5-bromopyridine (4.31 g).

NMR (DMSO-d$_6$, δ): 5.24 (2H, s), 6.64 (1H, m), 6.8–6.9 (2H, m), 7.14 (1H, t, J=8Hz), 8.19 (1H, t, J=2Hz), 8.66 (1H, d, J=2Hz), 8.78 (1H, d, J=2Hz).

PREPARATION 4

The following compound was obtained according to a similar manner to that of Preparation 3.

(1) 3-(3-Acetamidophenyl)aniline

NMR (DMSO-d$_6$, δ): 2.05 (3H, s), 5.17 (2H, s), 6.54 (1H, m), 6.70 (1H, m), 6.80 (1H, m), 7.10 (1H, dd, J=8, 8Hz), 7.20 (1H, m), 7.32 (1H, dd, J=8, 8Hz), 7.50 (1H, m), 7.82 (1H, m)

MASS (m/z): 227 (M+1).

(2) 2-(3-Aminophenyl)-6-methoxynaphthalene

NMR (DMSO-d$_6$, δ): 3.89 (3H, s), 5.16 (2H, s), 6.56 (1H, m), 6.90 (1H, m), 6.96 (1H, m), 7.12 (1H, d, J=8Hz), 7.18 (1H, dd, J=8, 2Hz), 7.33 (1H, m), 7.69 (1H, m), 7.88 (2H, m), 8.00 (1H, m).

PREPARATION 5

A mixture of 3-[(E)-2-(6-acetamido-3-pyridyl)vinyl] nitrobenzene (3.0 g), iron powder (1.48 g) and ammonium chloride (0.57 g), ethanol (30 ml) and water (9 ml) was stirred under reflux for 5 hours. The reaction was filtered, concentrated and extracted with chloroform. The extracts were chromatographed on silica gel (20 g, chloroform-methanol 100:1 as eluent) to give an oil. Crystallization from methanol afforded 3-[(E)-2-(6 -acetamido-3-pyridyl)vinyl] aniline (2.4 g).

NMR (DMSO-$d_6$, δ): 2.10 (3H, s), 5.10 (2H, s), 6.50 (1H, m), 6.73 (2H, m), 7.05 (3H, m), 8.05 (2H, m), 8.48 (1H, m).

PREPARATION 6

A mixture of 3-bromo-5-[(E)-2-(3-nitrophenyl)vinyl] pyridine (5.55 g), iron powder (3.05 g) and ammonium formate (5.73 g) in ethanol (90 ml) and water (30 ml) was stirred at 90þC. for 30 minutes. The mixture was filtered while hot. The filtrate was added to sodium bicarbonate solution and extracted with ethyl acetate twice. The combined organic solution was washed with sodium bicarbonate solution and brine, dried over magnesium sulfate and concentrated to give 3-[(E)-2-(3-aminophenyl)vinyl]-5-bromopyridine (3.57 g).

NMR (DMSO-$d_6$, δ): 5.13 (2H, s), 6.54 (1H, d, J=8Hz), 6.79 (2H, m), 7.0–7.1 (2H, m), 7.37 (1H, d, J=16Hz), 8.35 (1H, d, J=2Hz), 8.56 (1H, d, J=2Hz), 8.74 (1H, s).

PREPARATION 7

A mixture of 3-vinylaniline (8 g), 2-chloro-3-nitropyridine (10.7 g) and potassium carbonate (18.6 g) in dioxane (80 ml) was stirred under reflux for 5 days. The reaction was extracted with chloroform, washed with water, dried over magnesium sulfate and evaporated. After evaporation of the solvent, crude residue was crystallized from methanol to give 2-(3-vinylphenylamino)-3-nitropyridine as an orange crystals (12.9 g).

NMR (CDCl$_3$, δ): 5.30 (1H, d, J=12Hz), 5.79 (1H, d, J=16Hz), 6.75 (1H, dd, J=16, 12Hz), 6.85 (1H, dd, J=8, 4Hz), 7.25 (2H, m), 7.36 (1H, dd, J=8, 8Hz), 7.58 (1H, m), 7.67 (1H, s), 8.52 (2H, m).

PREPARATION 8

A mixture of 3-[(E)-2-(3-aminophenyl)vinyl]-5-bromopyridine (3.5 g), 2-chloro-3-nitropyridine (2.22 g) and potassium carbonate (2.64 g) in 1,4-dioxane (30 ml) was stirred under reflux for 22 hours. The mixture was filtered and the filtrate was concentrated. The resultant solid was washed with ethanol to give 2-[3-[(E)-2-(5-bromo pyridin-3-yl)vinyl]phenylamino]-3-nitropyridine (1.63 g).

NMR (CDCl$_3$, δ): 6.89 (1H, dd, J=5, 8Hz), 7.03 (1H, d, J=16Hz), 7.20 (1H, d, J=16Hz), 7.3–7.5 (2H, m), 7.60 (1H, d, J=8Hz), 7.87 (1H, s), 8.00 (1H, s), 8.5–8.6 (2H, m), 8.63 (1H, s).

PREPARATION 9

The following compounds were obtained according to a similar manner to that of Preparation 7 or 8.

(1) 2-[3-[(E)-2-(6-Acetamido-3-pyridyl)vinyl] phenylamino]-3-nitropyridine

NMR (DMSO-$d_6$, δ): 2.10 (3H, s), 7.00 (1H, dd, J=8, 5Hz), 7.22 (1H, d, J=16Hz), 7.30 (1H, d, J=16Hz), 7.39 (2H, m), 7.60 (1H, m), 7.84 (1H, m), 8.06 (2H, m), 8.53 (3H, m).

(2) 2-[3-(5-Bromopyridin-3-yl)phenylamino]-3-nitropyridine

NMR (CDCl$_3$, δ): 6.90 (1H, dd, J=5, 8Hz), 7.38 (1H, d, J=8Hz), 7.52 (1H, t, J=8Hz), 7.69 (1H, d, J=8Hz), 7.98 (1H, m), 8.07 (1H, t, J=2Hz), 8.5–8.6 (2H, m), 8.69 (1H, d, J=2Hz), 8.80 (1H, d, J=2Hz).

(3) 2-[3-(3-Acetamidophenyl)phenylamino]-3-nitropyridine

NMR (CDCl$_3$, δ): 2.20 (3H, s), 6.83 (1H, dd, J=8, 5Hz), 7.3–7.4 (4H, m), 7.45 (1H, dd, J=8, 8Hz), 7.52 (1H, m), 7.67 (1H, m), 7.75 (1H, s), 7.83 (1H, m), 8.52 (2H, m).

(4) 2-[3-(2-Methylbenzothiazol-6-yl)phenylamino]-3-nitropyridine

NMR (DMSO-$d_6$, δ): 2.80 (3H, s), 7.00 (1H, dd, J=8, 5Hz), 7.50 (2H, m), 7.75 (2H, m), 7.96 (2H, m), 8.35 (1H, s), 8.55 (2H, m).

(5) 2-[3-(2-Methylbenzothiazol-5-yl)phenylamino]-3-nitropyridine

NMR (DMSO-$d_6$, δ): 2.81 (3H, s), 7.01 (1H, dd, J=8, 5Hz), 7.50 (2H, m), 7.72 (2H, m), 8.02 (1H, s), 8.12 (1H, d, J=8Hz), 8.21 (1H, s), 8.53 (2H, m).

(6) 2-[3-(6-Methoxy-2-naphthyl)phenylamino]-3-nitropyridine

NMR (DMSO-$d_6$, δ): 3.90 (3H, s), 7.01 (1H, m), 7.20 (1H, m), 7.37 (1H, m), 7.50 (1H, dd, J=8, 8Hz), 7.57 (1H, m), 7.73 (1H, m), 7.84 (1H, m), 7.93 (2H, m), 8.04 (1H, m), 8.18 (1H, s), 8.56 (2H, m).

PREPARATION 10

A mixture of 2-(3-vinylphenylamino)-3-nitropyridine (12.9 g), 3-bromopyridine (12.7 g), palladium(II) acetate (0.24 g), copper(I) iodide (0.10 g), tri-o-tolylphosphine (0.65 g), triethylamine (25 ml) and acetonitrile (150 ml) was stirred under reflux under nitrogen overnight. After removal of the solvents, crude residue was chromatographed on silica gel (450 g, chloroform as eluent) to give 2-[3-[(E)-2-(3-pyridyl)vinyl]phenylamino]-3-nitropyridine as a reddish orange crystals (11.5 g).

NMR (DMSO-$d_6$, δ): 7.02 (1H, dd, J=8, 5Hz), 7.30 (1H, d, J=16Hz), 7.40 (4H, m), 7.65 (1H, m), 7.88 (1H, m), 8.05 (1H, d, J=8Hz), 8.46 (1H, m), 8.55 (2H, m), 8.80 (1H, m).

PREPARATION 11

The following compound was obtained according to a similar manner to that of Preparation 10.

2-[3-[(E)-2-(5-Methoxycarbonylpyridin-3-yl)vinyl] phenylamino]-3-nitropyridine

NMR (DMSO-$d_6$, δ): 3.92 (3H, s), 7.02 (1H, dd, J=8, 5Hz), 7.42 (3H, m), 7.56 (1H, d, J=16Hz), 7.68 (1H, m), 7.93 (1H, m), 8.55 (3H, m), 8.95 (1H, br s), 9.05 (1H, br s).

PREPARATION 12

A mixture of 2-[3-[(E)-2-(5-bromopyridin-3-yl)vinyl] phenylamino]-3-nitropyridine (800 mg), 4-vinylpyridine (233 mg), palladium(II) acetate (27 mg), tetra-n-butylammonium chloride (616 mg) and sodium bicarbonate (432 mg) in N,N-dimethylformamide (4 ml) was stirred at 120þC. for 4 hours. The mixture was poured into sodium bicarbonate solution and extracted with ethyl acetate twice. The combined organic solution was washed with aqueous sodium bicarbonate and brine, dried over magnesium sulfate and concentrated. The residue was crystallized from ethanol to give 2-[3-[(E)-2-[5-[(E)-2-(4-pyridyl)vinyl]pyridin-3-yl] vinyl]phenylamino]-3-nitropyridine (346 mg).

NMR (CDCl$_3$, δ): 6.89 (1H, dd, J=5, 8Hz), 7.1–7.5 (8H, m), 7.62 (1H, d, J=8Hz), 7.87 (1H, s), 8.00 (1H, s), 8.5–8.7 (6H, m).

PREPARATION 13

The following compounds were obtained according to a similar manner to that of Preparation 12.

(1) 2-[3-[(E)-2-[5-[(E)-2-Methoxycarbonylvinyl]pyridin-3-yl]vinyl]phenylamino]-3-nitropyridine NMR (CDCl$_3$, δ): 3.83 (3H, s), 6.59 (1H, d, J=16Hz), 6.89 (1H, dd, J=5, 8Hz), 7.11 (1H, d, J=16Hz), 7.23 (1H, d, J=16Hz), 7.3–7.45 (2H, m), 7.61 (1H, d, J=8Hz), 7.72 (1H, d, J=16Hz), 7.88 (1H, s), 7.96 (1H, t, J=2Hz), 8.5–8.6 (2H, m), 8.62 (1H, d, J=2Hz), 8.73 (1H, d, J=2Hz).

(2) 2-[3-[5-[(E)-2-(4-Pyridyl)vinyl]pyridin-3-yl]phenylamino]-3-nitropyridine

NMR (CDCl$_3$, δ): 6.90 (1H, dd, J=5, 8Hz), 7.15–7.6 (6H, m), 7.52 (1H, dt, J=8, 2Hz), 7.96 (1H, t, J=2Hz), 8.06 (1H, t, J=2Hz), 8.5–8.7 (4H, m), 8.76 (1H, d, J=2Hz), 8.82 (1H, d, J=2Hz), 10.25 (1H, s).

PREPARATION 14

The mixture of 2-[3-(6-methoxy-2-naphthyl)phenylamino]-3-nitropyridine (5.2 g), N-bromosuccinimide (3.24 g) and benzoylperoxide (678 mg) in chloroform (30 ml) was refluxed for 3 hours. The mixture was concentrated in vacuo and was purified by column chromatography (silica gel) to obtain 2-[3-(5-bromo-6-methoxy-2-naphthyl)phenylamino]-3-nitropyridine (3.3 g).

NMR (CDCl$_3$, δ): 4.05 (3H, s), 6.87 (1H, dd, J=8, 6Hz), 7.31 (1H, d, J=8Hz), 7.48–7.53 (2H, m), 7.65–7.73 (1H, m), 7.83–7.90 (2H, m), 7.95 (1H, s), 8.00 (1H, s), 8.29 (1H, d, J=8Hz), 8.45–8.56 (2H, m).

PREPARATION 15

A solution of 2-[3-(3-acetamidophenyl)phenylamino]-3-nitropyridine (10 g) in 3N hydrochloric acid (100 ml) was refluxed for 2 hours. The cold reaction was adjusted to pH 8 with saturated sodium bicarbonate solution and precipitated reddish crystals were collected, washed with water and dried to give 2-[3-(3-aminophenyl)phenylamino]-3-nitropyridine (9.53 g).

NMR (DMSO-d$_6$, δ): 6.89 (1H, m), 7.01 (1H, dd, J=8, 5Hz), 7.17 (2H, m), 7.30 (1H, m), 7.36 (1H, m), 7.45 (1H, dd, J=8, 8Hz), 7.68 (1H, m), 7.88 (1H, m), 8.55 (2H, m).

PREPARATION 16

To an ice cooled suspension of 3-(2-pyridyl)acrylic acid (1.07 g) in dry methylene chloride (80 ml) was added triethylamine (1.46 g) and pivaloyl chloride (0.87 g) and the mixture was stirred for 2 hours. After the clear reaction mixture was obtained, 2-[3-(3-aminophenyl)phenylamino]-3-nitropyridine (2.0 g) was added thereto and stirred under reflux overnight. The reaction was chromatographed on silica gel (chloroform-methanol 50:1 as an eluent) to give 2-[3-[3-[(E)-3-(2-pyridyl)acryloylamino]phenyl]phenylamino]-3-nitropyridine as an orange crystal (2.85 g).

NMR (DMSO-d$_6$, δ): 7.02 (1H, dd, J=8, 5Hz), 7.35 (1H, d, J=16Hz), 7.42 (4H, m), 7.50 (1H, m), 7.65 (2H, m), 7.71 (2H, m), 7.88 (1H, m), 7.94 (1H, s), 8.08 (1H, s), 8.55 (2H, m), 8.66 (1H, m).

PREPARATION 17

The following compounds were obtained according to a similar manner to that of Preparation 16.

(1) 2-[3-[3-[(E)-3-(6-Acetamido-3-pyridyl)acryloylamino]phenyl]phenylamino]-3-nitropyridine NMR (DMSO-d$_6$, δ): 2.11 (3H, s), 6.84 (1H, d, J=16Hz), 7.01 (1H, dd, J=8, 5Hz), 7.35–7.50 (4H, m), 7.60 (1H, d, J=16Hz), 7.70 (2H, m), 7.91 (1H, m), 8.05 (2H, m), 8.18 (1H, m), 8.55 (3H, m).

(2) 2-[3-[3-[(E)-3-(4-Pyridyl)acryloylamino]phenyl]phenylamino]-3-nitropyridine

NMR (DMSO-d$_6$, δ): 7.02 (1H, dd, J=8, 5Hz), 7.05 (1H, d, J=15Hz), 7.45 (4H, m), 7.60 (3H, m), 7.72 (2H, m), 7.93 (1H, m), 8.05 (1H, m), 8.55 (2H, m), 8.65 (2H, m).

PREPARATION 18

To a solution of 3-nitro-2-[3-[(E)-2-(3-pyridyl)vinyl]phenylamino]pyridine (2.22 g) in dichloromethane (70 ml) was added m-chloroperbenzoic acid (1.81 g). The mixture was stirred at room temperature for 1 hour, then poured into aqueous sodium bicarbonate and extracted with chloroform. The organic solution was washed with aqueous sodium bicarbonate and brine, dried over magnesium sulfate and concentrated. The residue was chromatographed on silica gel column (8% methanol in chloroform) to give 3-nitro-2-[3-[(E)-2-(1-oxido-3-pyridyl)vinyl]phenylamino]pyridine (1.51 g).

NMR (CDCl$_3$, δ): 6.85–7.0 (2H, m), 7.15–7.5 (5H, m), 7.62 (1H, d, J=8Hz), 7.88 (1H, s), 8.12 (1H, d, J=5Hz), 8.38 (1H, s), 8.5–8.6 (2H, m).

PREPARATION 19

The following compounds were obtained according to a similar manner to that of Preparation 18.

(1) 3-Nitro-2-[3-[(E)-2-(1-oxido-4-pyridyl)vinyl]phenylamino]pyridine

NMR (CDCl$_3$, δ): 6.89 (1H, dd, J=5, 8Hz), 7.01 (1H, d, J=16Hz), 7.20 (1H, d, J=16Hz), 7.3–7.5 (4H, m), 7.84 (1H, s), 8.19 (1H, d, J=7Hz), 8.5–8.6 (2H, m).

(2) 2-[3-[3-[(E)-3-(1-Oxido-4-pyridyl)acryloylamino]phenyl]phenylamino]-3-nitropyridine NMR (DMSO-d$_6$, δ): 6.90 (1H, d, J=16Hz), 7.01 (1H, dd, J=8, 5Hz), 7.45 (4H, m), 7.57 (1H, d, J=16Hz), 7.65 (2H, m), 7.70 (2H, m), 7.92 (1H, s), 8.03 (1H, s), 8.25 (2H, m), 8.55 (2H, m).

PREPARATION 20

A mixture of 2-[3-[(E)-2-(2-acetamido-3-pyridyl)vinyl]phenylamino]-3-aminopyridine (1.86 g), iron powder (1.39 g) and ammonium chloride (0.26 g), ethanol (20 ml) and water (6 ml) was stirred under reflux for an hour. The reaction was filtered, concentrated and extracted with chloroform. The extracts were washed with saturated sodium bicarbonate solution, dried and evaporated to afford 2-[3-[(E)-2-(6-acetamido-3-pyridyl)vinyl]phenylamino]-3-aminopyridine as dark purple crystals (1.59 g).

NMR (DMSO-d$_6$, δ): 2.10 (3H, s), 5.08 (2H, s), 6.64 (1H, dd, J=8, 5Hz), 6.90 (1H, d, J=8Hz), 7.11 (2H, m), 7.23 (2H, m), 7.55 (2H, m), 7.77 (2H, m), 8.07 (2H, s), 8.50 (1H, s).

PREPARATION 21

A mixture of 2-[3-[(E)-2-[5-[(E)-2-(4-pyridyl)vinyl]pyridin-3-yl]vinyl]phenylamino]-3-nitropyridine (331 mg), iron powder (132 mg) and ammonium formate (297 mg) in ethanol (6 ml) and water (2 ml) was stirred at 90þC. for 30 minutes. The mixture was filtered while hot. The filtrate was added to aqueous sodium bicarbonate solution and extracted with ethyl acetate twice. The combined organic solution was washed with sodium bicarbonate and brine, dried over magnesium sulfate and concentrated. The resultant solid was washed with diisopropyl ether to give 3-amino-2-[3-[(E)-2-

[5-[(E)-2-(4-pyridyl)vinyl]pyridin-3-yl]vinyl]phenylamino]pyridine (270 mg).

NMR (DMSO-d$_6$, δ): 5.10 (2H, s), 6.67 (1H, dd, J=5, 8Hz), 6.92 (1H, d, J=8Hz), 7.1–7.3 (3H, m), 7.4–7.7 (7H, m), 7.81 (1H, s), 7.90 (1H, s), 8.42 (1H, s), 8.61 (1H, d, J=5Hz), 8.69 (1H, s), 8.72 (1H, s).

PREPARATION 22

The following compounds were obtained according to a similar manner to that of Preparation 20 or 21.

(1) 2-[3-[3-[(E)-3-(2-Pyridyl)acryloylamino]phenyl]phenylamino]-3-aminopyridine

NMR (DMSO-d$_6$, δ): 6.75 (1H, m), 7.0–8.2 (15H, m), 8.65 (1H, m).

(2) 2-[3-[3-[(E)-3-(6-Acetamido-3-pyridyl)acryloylamino]phenyl]phenylamino]-3-aminopyridine NMR (DMSO-d$_6$, δ): 2.12 (3H, s), 5.10 (2H, br s), 6.65 (1H, m), 6.88 (2H, m), 7.11 (1H, m), 7.38 (3H, m), 7.60 (4H, m), 7.88 (1H, m), 8.04 (2H, m), 8.15 (1H, m), 8.55 (1H, m).

(3) 3-Amino-2-[3-[(E)-2-[5-[(E)-2-methoxycarbonylvinyl]pyridin-3-yl]vinyl]phenylamino]pyridine NMR (DMSO-d$_6$, δ): 3.77 (3H, s), 5.09 (2H, s), 6.65 (1H, dd, J=5, 8Hz), 6.9–7.0 (2H, m), 7.1–7.3 (3H, m), 7.45–7.6 (3H, m), 7.7–7.9 (3H, m), 8.52 (1H, s), 8.76 (2H, m).

(4) 3-Amino-2-[3-[5-[(E)-2-(4-pyridyl)vinyl]pyridin-3-yl]phenylamino]pyridine

NMR (DMSO-d$_6$, δ): 5.11 (2H, s), 6.67 (1H, dd, J=5, 8Hz), 7.94 (1H, dd, J=2, 8Hz), 7.26 (1H, d, J=8Hz), 7.40 (1H, t, J=8Hz), 7.5–7.7 (5H, m), 7.80 (1H, d, J=8Hz), 7.9–8.0 (2H, m), 8.32 (1H, s), 8.60 (1H, d, J=5Hz), 8.78 (1H, d, J=2Hz), 8.82 (1H, d, J=2Hz).

(5) 3-Amino-2-[3-[(E)-2-(1-oxido-3-pyridyl)vinyl]phenylamino]pyridine

NMR (DMSO-d$_6$, δ): 5.10 (2H, s), 6.64 (1H, dd, J=5, 8Hz), 6.92 (1H, d, J=8Hz), 7.1–7.7 (8H, m), 7.81 (2H, m), 8.11 (1H, d, J=5Hz), 8.53 (1H, s).

(6) 3-Amino-2-[3-[(E)-2-(1-oxido-4-pyridyl)vinyl]phenylamino]pyridine

NMR (DMSO-d$_6$, δ): 5.10 (2H, s), 6.66 (1H, dd, J=5, 8Hz), 6.92 (1H, d, J=8Hz), 7.1–7.2 (2H, m), 7.28 (1H, t, J=8Hz), 7.37 (1H, d, J=16Hz), 7.5–7.7 (4H, m), 7.8–7.9 (2H, m), 8.19 (1H, d, J=5Hz).

(7) 2-[3-(3-Acetamidophenyl)phenylamino]-3-aminopyridine

NMR (CDCl$_3$, δ): 2.13 (3H, s), 3.50 (2H, br s), 6.33 (1H, s), 6.77 (1H, dd, J=8, 5Hz), 7.00 (1H, d, J=8Hz), 7.12 (1H, dd, J=8, 2Hz), 7.2–7.4 (5H, m), 7.50 (1H, m), 7.55 (1H, m), 7.61 (1H, s), 7.82 (1H, d, J=5Hz).

(8) 2-[3-[3-[(E)-3-(1-Oxido-4-pyridyl)acryloylamino]phenyl]phenylamino]-3-aminopyridine NMR (DMSO-d$_6$, δ): 5.10 (2H, s), 6.64 (1H, dd, J=8, 5Hz), 6.90 (1H, d, J=15Hz), 6.93 (1H, d, J=8Hz), 7.10 (1H, d, J=8Hz), 7.35 (2H, m), 7.45 (1H, dd, J=8, 8Hz), 7.53 (1H, d, J=5Hz), 7.58 (1H, d, J=15Hz), 7.67 (4H, m), 7.90 (2H, d, J=8Hz), 8.00 (1H, m), 8.26 (2H, d, J=8Hz).

(9) 2-[3-(2-Methylbenzothiazol-5-yl)phenylamino]-3-aminopyridine

NMR (DMSO-d$_6$, δ): 2.80 (3H, s), 5.12 (2H, s), 6.64 (1H, m), 6.92 (1H, m), 7.20 (1H, m), 7.35 (1H, m), 7.52 (1H, m), 7.65 (1H, m), 7.71 (1H, m), 7.92 (1H, m), 8.00 (1H, m), 8.10 (2H, m).

(10) 2-[3-(2-Methylbenzothiazol-6-yl)phenylamino]-3-aminopyridine

NMR (DMSO-d$_6$, δ): 2.80 (3H, s), 5.15 (2H, s), 6.65 (1H, m), 6.95 (1H, m), 7.25 (1H, m), 7.35 (1H, m), 7.55 (1H, m), 7.75 (2H, m), 8.00 (3H, m), 8.30 (1H, m).

(11) 2-[3-[(E)-2-(5-Methoxycarbonylpyridin-3-yl)vinyl]phenylamino]-3-aminopyridine NMR (DMSO-d$_6$, δ): 3.92 (3H, s), 5.10 (2H, s), 6.65 (1H, dd, J=8, 5Hz), 6.92 (1H, d, J=8Hz), 7.18 (1H, m), 7.28 (2H, m), 7.50 (1H, d, J=16Hz), 7.54 (1H, m), 7.60 (1H, m), 7.80 (1H, s), 7.88 (1H, m), 8.50 (1H, m), 8.94 (1H, s), 9.05 (1H, d, J=3Hz).

(12) 2-[3-(6-Methoxy-2-naphthyl)phenylamino]-3-aminopyridine

NMR (CDCl$_3$, δ): 3.45 (2H, br s), 3.93 (3H, s), 6.30 (1H, s), 6.80 (1H, dd, J=8, 5Hz), 7.04 (1H, m), 7.16 (2H, m), 7.30 (2H, m), 7.39 (1H, m), 7.54 (1H, m), 7.71 (1H, m), 7.79 (2H, m), 7.87 (1H, m), 7.98 (1H, s).

(13) 2-[3-(5-Bromo-6-methoxy-2-naphthyl)phenylamino]-3-aminopyridine

NMR (CDCl$_3$, δ): 3.45 (1H, br s), 4.03 (3H, s), 6.34 (1H, br s), 6.79 (1H, dd, J=6, 8Hz), 7.02 (1H, dd, J=8, 8Hz), 7.25–7.33 (4H, m), 7.35–7.40 (1H, m), 7.57 (1H, m), 7.79–7.87 (3H, m), 7.95 (1H, s), 8.25 (1H, m)

MASS (m/z): 420 (M+1), 422.

PREPARATION 23

The mixture of 2-[3-(6-methoxy-2-naphthyl)phenylamino]-3-aminopyridine (60 g) and pyruvic acid (18.6 g) in methanol was refluxed for 5 hours. The mixture was cooled and crystallized. 2-Methyl-4-[3-(6-methoxy-2-naphthyl)phenyl]-3-oxo-3,4-dihydropyrido[2,3-b]pyridine (12.6 g) was collected by suction.

NMR (DMSO-d$_6$, δ): 2.51 (3H, s), 3.88 (3H, s), 7.20 (1H, m), 7.35 (2H, m), 7.40 (1H, dd, J=8, 5Hz), 7.66 (1H, dd, J=8, 8Hz), 7.81 (2H, m), 7.90 (3H, m), 8.19 (1H, s), 8.23 (1H, m), 8.40 (1H, m).

PREPARATION 24

The following compound was obtained according to a similar manner to that of Preparation 23.

4-[3-(3-Acetamidophenyl)phenyl]-2-(3-pyridylmethyl)-3-oxo-3,4-dihydropyrido[2,3-b]pyrazine mp: 190–193þC.

NMR (CDCl$_3$, δ): 2.13 (3H, s), 4.32 (2H, s), 7.2–7.35 (5H, m), 7.45 (2H, m), 7.55 (1H, s), 7.62 (1H, dd, J=8, 8Hz), 7.70 (2H, m), 7.82 (1H, m), 8.18 (1H, d, J=8Hz), 8.41 (1H, m), 8.49 (1H, d, J=5Hz), 8.73 (1H, s).

PREPARATION 25

The mixture of 2-methyl-4-[3-(6-methoxy-2-naphthyl)phenyl]-3-oxo-3,4-dihydropyrido[2,3-b]pyrazine (3.4 g), N-bromosuccinimide (3.08 g) and benzoylperoxide (837 mg) in chloroform (30 ml) was refluxed for 3 hours. The mixture was concentrated in vacuo and was purified by column chromatography (silica gel) to obtain 2-bromomethyl-4-[3-(6-methoxy-5-bromo-2-naphthyl)phenyl]-3-oxo-3,4-dihydropyrido[2,3-b]pyrazine (2.2 g).

NMR (CDCl$_3$, δ): 4.04 (3H, s), 4.71 (2H, s), 7.25–7.40 (3H, m), 7.65 (1H, m), 7.72 (1H, dd, J=8, 8Hz), 7.85 (3H, m), 8.02 (1H, s), 8.27 (2H, m), 8.50 (1H, m)

MASS (m/z): 550 (M+1), 552, 554.

PREPARATION 26

The following compounds were obtained according to a similar manner to that of Preparation 15.

4-[3-(3-Aminophenyl)phenyl]-2-(3-pyridylmethyl)-3-oxo-3,4-dihydropyrido[2,3-b]pyrazine mp: 202–204þC.

NMR (CDCl$_3$, δ): 3.73 (2H, s), 4.32 (2H, s), 6.15 (1H, m), 6.90 (1H, m), 6.98 (1H, d, J=8Hz), 7.25 (4H, m), 7.44 (1H, s), 7.62 (1H, dd, J=8, 8Hz), 7.70 (1H, d, J=8Hz), 7.82 (1H, d, J=8Hz), 8.18 (1H, d, J=8Hz), 8.43 (1H, d, J=5Hz), 8.50 (1H, m), 8.72 (1H, s).

EXAMPLE 1

A mixture of 3-amino-2-[3-[(E)-2-[5-[(E)-2-(4-pyridyl)vinyl]pyridin-3-yl]vinyl]phenylamino]pyridine (260 mg) and 3-pyridylpyruvic acid (121 mg) in ethanol (5 ml) was stirred under reflux for 5 hours. After removal of the solvent, the residue was chromatographed on silica gel column (chloroform-methanol, 9:1) and crystallized from methanol to give 2-(3-pyridylmethyl)-3-oxo-4-[3-[(E)-2-[5-[(E)-2-(4-pyridyl)vinyl]pyridin-3-yl]vinyl]phenyl]-3,4-dihydropyrido[2,3-b]pyrazine (208 mg).

NMR (CDCl$_3$, δ): 4.33 (2H, s), 7.1–7.35 (7H, m), 7.40 (2H, d, J=5Hz), 7.47 (1H, s), 7.55–7.7 (2H, m), 7.83 (1H, d, J=8Hz), 7.95 (1H, s), 8.20 (1H, d, J=8Hz), 8.44 (1H, d, J=5Hz), 8.52 (1H, d, J=5Hz), 8.6–8.7 (4H, m), 8.74 (1H, s).

EXAMPLE 2

A suspension of 2-[3-[(E)-2-(6-acetamido-3-pyridyl)vinyl]phenylamino]-3-aminopyridine (1.5 g) and 3-pyridylpyruvic acid (0.79 g) in ethanol (30 ml) was stirred under reflux for 8 hours. The cold reaction mixture was filtered and washed with ethanol to give 2-(3-pyridylmethyl)-3-oxo-4-[3-[(E)-2-(6-acetamido-3-pyridyl)vinyl]phenyl]-3,4-dihydropyrido[2,3-b]pyrazine as colorless crystals (1.76 g).

mp: 260–261þC.

NMR (DMSO-d$_6$, δ): 2.10 (3H, s), 4.25 (2H, s), 7.27 (3H, m), 7.39 (2H, m), 7.58 (2H, m), 7.68 (1H, m), 7.78 (1H, m), 8.05 (2H, m), 8.22 (1H, m), 8.40 (1H, m), 8.45 (2H, m), 8.59 (1H, m)

EXAMPLE 3

The following compounds were obtained according to a similar manner to that of Example 1 or 2.

(1) 2-(3-Pyridylmethyl)-4-[3-[5-[(E)-2-(4-pyridyl)vinyl]pyridin-3-yl]phenyl]-3-oxo-3,4-dihydropyrido[2,3-b]pyrazine mp: 253–257þC.

NMR (CDCl$_3$, δ): 4.32 (2H, s), 7.13 (1H, d, J=16Hz), 7.2–7.4 (6H, m), 7.53 (1H, m), 7.7–7.85 (3H, m), 8.03 (1H, t, J=2Hz), 8.21 (1H, dd, J=2, 8Hz), 8.43 (1H, dd, J=2, 5Hz), 8.51 (1H, dd, J=2, 5Hz), 8.61 (2H, d, J=5Hz), 8.73 (2H, t, J=2Hz), 8.80 (1H, d, J=2Hz).

(2) 4-[3-[3-[(E)-3-(2-Pyridyl)acryloylamino]phenyl]phenyl]-2-(3-pyridylmethyl)-3-oxo-3,4-dihydropyrido[2,3-b]pyrazine mp: 195–211þC.

NMR (DMSO-d$_6$, δ): 4.27 (2H, s), 7.3–7.5 (8H, m), 7.6–7.8 (7H, m), 7.86 (1H, dd, J=8, 8Hz), 8.05 (1H, m), 8.21 (1H, m), 8.40 (1H, m), 8.46 (1H, m), 8.60 (1H, m), 8.63 (1H, m).

(3) 4-[3-[3-[(E)-3-(6-Acetamido-3-pyridyl)acryloylamino]phenyl]phenyl]-2-(3-pyridylmethyl)-3-oxo-3,4-dihydropyrido[2,3-b]pyrazine mp: 233–237þC.

NMR (DMSO-d$_6$, δ): 2.11 (3H, s), 4.27 (2H, s), 6.80 (1H, d, J=16Hz), 7.40 (5H, m), 7.57 (1H, d, J=16Hz), 7.68 (3H, m), 7.78 (2H, m), 8.04 (2H, m), 8.19 (2H, m), 8.41 (1H, m), 8.45 (1H, m), 8.53 (1H, m), 8.60 (1H, m).

(4) 2-(3-Pyridylmethyl)-4-[3-[(E)-2-[5-[(E)-2-methoxycarbonylvinyl]pyridin-3-yl]vinyl]phenyl]-3-oxo-3,4-dihydropyrido[2,3-b]pyrazine mp: 196–199þC.

NMR (CDCl$_3$, δ): 3.82 (3H, s), 4.31 (2H, s), 6.56 (1H, d, J=16Hz), 7.09 (1H, d, J=16Hz), 7.2–7.35 (4H, m), 7.45 (1H, s), 7.55–7.75 (3H, m), 7.82 (1H, dd, J=2, 8Hz), 7.90 (1H, d, J=2Hz), 8.20 (1H, dd, J=2, 8Hz), 8.44 (1H, m), 8.51 (1H, m), 8.61 (1H, s), 8.69 (1H, s), 8.73 (1H, s).

(5) 2-(3-Pyridylmethyl)-4-[3-[(E)-2-(1-oxido-3-pyridyl)vinyl]phenyl]-3-oxo-3,4-dihydropyrido[2,3-b]pyrazine NMR (CDCl$_3$, δ): 6.89 (1H, dd, J=5, 8Hz), 7.01 (1H, d, J=16Hz), 7.20 (1H, d, J=16Hz), 7.3–7.5 (4H, m), 7.84 (1H, s), 8.19 (1H, d, J=7Hz), 8.5–8.6 (2H, m).

(6) 2-(3-Pyridylmethyl)-4-[3-[(E)-2-(1-oxido-4-pyridyl)vinyl]phenyl]-3-oxo-3,4-dihydropyrido[2,3-b]pyrazine NMR (CDCl$_3$, δ): 4.32 (2H, s), 6.98 (1H, d, J=16Hz), 7.15–7.35 (6H, m), 7.42 (1H, s), 7.55–7.7 (2H, m), 7.82 (1H, d, J=8Hz), 8.1–8.25 (3H, m), 8.42 (1H, d, J=5Hz), 8.51 (1H, d, J=5Hz), 8.72 (1H, s).

(7) 4-[3-[3-[(E)-3-(1-Oxido-4-pyridyl)acryloylamino]phenyl]phenyl]-2-(3-pyridylmethyl)-3-oxo-3,4-dihydropyrido[2,3-b]pyrazine mp: 190–195þC.

NMR (DMSO-d$_6$, δ): 4.26 (2H, s), 6.87 (1H, d, J=16Hz), 7.3–7.5 (5H, m), 7.55 (1H, d, J=16Hz), 7.6–7.8 (7H, m), 8.01 (1H, s), 8.22 (3H, m), 8.40 (1H, d, J=5Hz), 8.47 (1H, d, J=5Hz), 8.60 (1H, s).

(8) 4-[3-(2-Methylbenzothiazol-5-yl)phenyl]-2-(3-pyridylmethyl)-3-oxo-3,4-dihydropyrido[2,3-b]pyrazine mp: 198–200þC.

NMR (DMSO-d$_6$, δ): 2.80 (3H, s), 4.28 (2H, s), 7.37 (3H, m), 7.65–7.72 (1H, m), 7.80 (2H, m), 7.91 (1H, m), 8.11 (1H, d, J=8Hz), 8.21 (2H, m), 8.42 (1H, d, J=5Hz), 8.46 (1H, d, J=5Hz), 8.60 (1H, s).

(9) 4-[3-(2-Methylbenzothiazol-6-yl)phenyl]-2-(3-pyridylmethyl)-3-oxo-3,4-dihydropyrido[2,3-b]pyrazine mp: 241–243þC.

NMR (DMSO-d$_6$, δ): 2.80 (3H, s), 4.27 (2H, s), 7.40 (3H, m), 7.65 (1H, dd, J=8, 8Hz), 7.80 (3H, m), 7.90 (1H, m), 7.97 (1H, d, J=8Hz), 8.22 (1H, dd, J=8, 2Hz), 8.38 (1H, d, J=2Hz), 8.40 (1H, m), 8.45 (1H, m), 8.60 (1H, d, J=2Hz).

(10) 4-[3-[(E)-2-(5-Methoxycarbonylpyridin-3-yl)vinyl]phenyl]-2-(3-pyridylmethyl)-3-oxo-3,4-dihydropyrido[2,3-b]pyrazine mp: 171–173þC.

NMR (DMSO-d$_6$, δ): 3.90 (3H, s), 4.26 (2H, s), 7.32 (1H, m), 7.40 (3H, m), 7.60 (2H, m), 7.68 (1H, s), 7.80 (2H, m), 8.22 (1H, d, J=8Hz), 8.42 (1H, m), 8.48 (2H, m), 8.60 (1H, s), 8.95 (1H, m), 9.00 (1H, m).

(11) 2-(3-Pyridylmethyl)-4-[3-(6-methoxy-5-bromo-2-naphthyl)phenyl]-3-oxo-3,4-dihydropyrido[2,3-b]pyrazine mp: 211–214þC.

NMR (CDCl$_3$, δ): 4.04 (3H, s), 4.34 (2H, s), 7.24–7.35 (4H, m), 7.60 (1H, m), 7.70 (1H, dd, J=8, 8Hz), 7.80–7.90

(4H, m), 8.00 (1H, m), 8.19 (1H, dd, J=8, 2Hz), 8.25 (1H, d, J=8Hz), 8.45 (1H, m), 8.50 (1H, m), 8.74 (1H, m).

EXAMPLE 4

To a solution of 2-(3-pyridylmethyl)-4-[3-[(E)-2-(3-pyridyl)vinyl]phenyl]-3-oxo-3,4-dihydropyrido[2,3-b]pyrazine (374 mg) in dichloromethane (20 ml) was added m-chloroperbenzoic acid (232 mg). The mixture was stirred in ice bath for 1 hour, then poured into aqueous sodium bicarbonate and extracted with chloroform. The organic solution was washed with aqueous sodium bicarbonate and brine, dried over magnesium sulfate and concentrated. The residue was chromatographed on silica gel column (chloroform-methanol, 9:1) to give 2-[(1-oxido-3-pyridyl)methyl]-4-[3-[(E)-2-(1-oxido-3-pyridyl)vinyl]phenyl]-3-oxo-3,4-dihydropyrido[2,3-b]pyrazine (43 mg).

NMR (CDCl$_3$, δ): 4.29 (2H, s), 6.92 (1H, d, J=16Hz), 7.15–7.45 (8H, m), 7.6–7.7 (2H, m), 8.13 (3H, m), 8.21 (1H, d, J=8Hz), 8.3–8.4 (2H, m), 8.48 (1H, dd, J=2, 5Hz).

EXAMPLE 5

To a solution of 4-[3-[(E)-2-(3,5-dichlorophenyl)vinyl]phenyl]-2-(3-pyridylmethyl)-3-oxo-3,4-dihydropyrido[2,3-b]pyrazine (255 mg) in dichloromethane (10 ml) was added m-chloroperbenzoic acid (181 mg). The mixture was stirred at room temperature for 1 hour, then poured into aqueous sodium bicarbonate and extracted with chloroform. The organic solution was washed with aqueous sodium bicarbonate and brine, dried over magnesium sulfate and concentrated. The resultant solid was washed with diisopropyl ether to give 4-[3-[(E)-2-(3,5-dichlorophenyl) vinyl] phenyl]-2-[(1-oxido-3-pyridyl)methyl]-3-oxo-3,4-dihydropyrido[2,3-b]pyrazine (167 mg).

NMR (CDCl$_3$, δ): 4.28 (2H, s), 6.97 (1H, d, J=16Hz), 7.1–7.45 (9H, m), 7.55–7.7 (2H, m), 8.12 (1H, d, J=5Hz), 8.20 (1H, d, J=8Hz), 8.36 (1H, s), 8.47 (1H, m).

EXAMPLE 6

The following compounds were obtained according to a similar manner to that of Example 4 or 5.

(1) 4-[3-(3-Acetamidophenyl)phenyl]-2-[(1-oxido-3-pyridyl)methyl]-3-oxo-3,4-dihydropyrido[2,3-b]pyrazine NMR (CDCl$_3$, δ): 2.16 (3H, s), 4.25 (2H, s), 7.24 (2H, m), 7.34 (3H, m), 7.43 (2H, m), 7.52 (1H, m), 7.64 (1H, dd, J=8, 8Hz), 7.69 (1H, m), 7.73 (2H, m), 8.12 (1H, m), 8.18 (1H, d, J=8Hz), 8.38 (1H, s), 8.45 (1H, d, J=5Hz)

(2) 2-[(1-Oxido-3-pyridyl)methyl]-4-[3-[(E)-2-(1-oxido-4-pyridyl)vinyl]phenyl]-3-oxo-3,4-dihydropyrido[2,3-b]pyrazine mp: 168–180þC.

NMR (CDCl$_3$, δ): 4.28 (2H, s), 6.99 (1H, d, J=16Hz), 7.15–7.45 (8H, m), 7.55–7.7 (2H, m), 8.1–8.25 (4H, m), 8.37 (1H, s), 8.47 (1H, m).

EXAMPLE 7

A solution of 4-[3-[(E)-2-(6-acetamido-3-pyridyl)vinyl]phenyl]-2-(3-pyridylmethyl)-3-oxo-3,4-dihydropyrido[2,3-b]pyrazine (1.56 g) in 4N hydrochloric acid (30 ml) was refluxed for an hour. The cold reaction was diluted with water and precipitated materials were collected, washed with water and dried to give 4-[3-[(E)-2-(6-amino-3-pyridyl)vinyl]phenyl]-2-(3-pyridylmethyl)-3-oxo-3,4-dihydropyrido[2,3-b]pyrazineþbdihydrochloride (1.65 g).

mp: 215–222þC.

NMR (DMSO-d$_6$, δ): 4.48 (2H, s), 7.08 (1H, d, J=8Hz), 7.20 (1H, d, J=16Hz), 7.28 (2H, m), 7.40 (1H, dd, J=8, 5Hz), 7.52 (1H, s), 7.58 (1H, dd, J=8, 8Hz), 7.66 (1H, d, J=8Hz), 8.02 (1H, dd, J=8, 5Hz), 8.06 (1H, s), 8.18 (1H, d, J=8Hz), 8.33 (3H, m), 8.42 (1H, d, J=5Hz), 8.52 (1H, d, J=8Hz), 8.83 (1H, d, J=5Hz), 8.92 (1H, s).

EXAMPLE 8

The following compound was obtained according to a similar manner to that of Example 7.

4-[3-(3-Aminophenyl)phenyl]-2-[(1-oxido-3-pyridyl)methyl]-3-oxo-3,4-dihydropyrido[2,3-b]pyrazine NMR (CDCl$_3$, δ): 4.27 (2H, s), 6.67 (1H, dd, J=8, 2Hz), 6.91 (1H, m), 6.99 (1H, d, J=8Hz), 7.22 (3H, m), 7.31 (1H, dd, J=8, 5Hz), 7.43 (2H, m), 7.63 (1H, dd, J=8, 8Hz), 7.72 (1H, m), 8.13 (1H, m), 8.18 (1H, d, J=8Hz), 8.36 (1H, s), 8.45 (1H, d, J=5Hz).

EXAMPLE 9

To a suspension of 4-[3-[(E)-2-(6-amino-3-pyridyl)vinyl] phenyl]-2-(3-pyridy lmethyl)-3-oxo-3,4-dihydropyrido[2,3-b]pyrazineþ bdihydrochloride (0.3 g) was added triethylamine (0.17 g) and bis(trifluoroacetyl)anhydride (0.14 g). The resulted mixture was stirred for additional 2 hours and precipitated colorless crystals were collected, washed with methylene chloride and dried to give 4-[3-[(E)-2-(6-trifluoroacetylamino-3-pyridyl)vinyl]phenyl]-2-(3-pyridylmethyl)-3-oxo-3,4-dihydropyrido[2,3-b]pyrazine (0.28 g).

mp: 155–163þC.

NMR (DMSO-d$_6$, δ): 4.40 (2H, s), 7.02 (1H, d, J=8Hz), 7.18 (1H, d, J=16Hz), 7.28 (2H, m), 7.41 (1H, dd, J=8, 5Hz), 7.53 (1H, s), 7.60 (1H, s), 7.68 (1H, m), 7.79 (1H, dd, J=8, 5Hz), 8.05 (1H, s) 8.20–8.35 (4H, m), 8.42 (1H, m), 8.71 (1H, m), 8.80 (1H, s).

EXAMPLE 10

To a solution of 4-(3-aminophenyl)-2-(3-pyridylmethyl)-3-oxo-3,4-dihydropyrido[2,3-b]pyrazine (300 mg) and triethylamine (0.33 ml) in 1,4-dioxane (10 ml) was added 5-bromo-3-pyridylcarbonyl chloride·hydrochloride (304 mg). The mixture was stirred at room temperature for 15 minutes, then poured into aqueous sodium bicarbonate and extracted with ethyl acetate. The organic solution was washed with aqueous sodium bicarbonate and brine, dried over magnesium sulfate and concentrated. The residue was crystallized from methanol to give 4-[3-[(5-bromo-3-pyridyl)carbonylamino]phenyl]-2-(3-pyridylmethyl)-3-oxo-3,4-dihydropyrido[2,3-b]pyrazine (256 mg).

mp: 223–226þC.

NMR (CDCl$_3$, δ): 4.32 (2H, s), 6.78 (1H, d, J=8Hz), 7.12 (1H, dd, J=5, 8Hz), 7.3–7.45 (2H, m), 7.56 (1H, s), 7.7–7.8 (2H, m), 8.2–8.3 (2H, m), 8.32 (1H, m), 8.43 (1H, m), 8.65 (1H, s), 8.74 (1H, d, J=2Hz), 8.88 (1H, s), 8.91 (1H, s).

EXAMPLE 11

The following compounds were obtained according to a similar manner to that of Example 10.

(1) 4-[3-[3-[(E)-3-(4-Chlorophenyl)acryloylamino]phenyl]phenyl]-2-(3-pyridylmethyl)-3-oxo-3,4-dihydropyrido[2,3-b]pyrazine mp: 187–193þC.

NMR (CDCl$_3$, δ): 4.33 (2H, s), 6.50 (1H, d, J=16Hz), 7.2–7.45 (8H, m), 7.47 (1H, m), 7.52 (1H, m), 7.62 (2H, m), 7.72 (2H, m), 7.84 (3H, m), 8.20 (1H, m), 8.42 (1H, m), 8.50 (1H, m), 8.75 (1H, s).

(2) 4-[3-[3-[(E)-3-(3-Chlorophenyl)propenoylamino]phenyl]phenyl]-2-(3-pyridylmethyl)-3-oxo-3,4-dihydropyrido[2,3-b]pyrazine mp: 214–217þC.

NMR (CDCl$_3$, δ): 4.33 (2H, s), 6.52 (1H, d, J=16Hz), 7.2–7.4 (8H, m), 7.50 (2H, m), 7.54 (1H, m), 7.65 (3H, m), 7.74 (1H, m), 7.85 (2H, m), 8.20 (1H, m), 8.43 (1H, m), 8.51 (1H, m), 8.75 (1H, m).

(3) 4-[3-[3-[(E)-3-(2-Chlorophenyl)propenoylamino]phenyl]phenyl]-2-(3-pyridylmethyl)-3-oxo-3,4-dihydropyrido[2,3-b]pyrazine mp: 225–230þC.

NMR (DMSO-d$_6$, δ): 4.27 (2H, s), 6.89 (1H, d, J=16Hz), 7.4 (8H, m), 7.55 (1H, m), 7.67 (3H, m), 7.79 (3H, m), 7.88 (1H, d, J=16Hz), 8.07 (1H, m), 8.20 (1H, m), 8.41 (1H, m), 8.46 (1H, m), 8.60 (1H, m).

(4) 4-[3-[3-[(E)-3-(3-Pyridyl)acryloylamino]phenyl]phenyl]-2-(3-pyridylmethyl)-3-oxo-3,4-dihydropyrido[2,3-b]pyrazine mp: 185–191þC.

NMR (DMSO-d$_6$, δ): 4.27 (2H, s), 7.03 (1H, d, J=16Hz), 7.40 (5H, m), 7.57 (3H, m), 7.75 (5H, m), 8.01 (1H, s), 8.21 (1H, m), 8.41 (1H, m), 8.47 (1H, m), 8.62 (3H, m).

(5) 4-[3-[3-[(E)-3-(4-Pyridyl)acryloylamino]phenyl]phenyl]-2-[(1-oxido-3-pyridyl)methyl]-3-oxo-3,4-dihydropyrido[2,3-b]pyrazine NMR (CDCl$_3$, δ): 4.28 (2H, s), 7.05 (1H, d, J=16Hz), 7.2–7.5 (9H, m), 7.62 (2H, m), 7.75 (2H, m), 7.95 (1H, m), 8.12 (1H, m), 8.19 (1H, m), 8.43 (2H, m), 8.60 (2H, m), 9.25 (1H, m)

MASS (m/z): 553 (M+1).

EXAMPLE 12

To a stirred suspension of 2-(3-pyridyl)thiazole-4-carboxylic acid (0.56 g) and triethylamine (0.55 g) in methylene chloride (25 ml) was added pivaloyl chloride (0.33 g) in methylene chloride (5 ml) and the mixture was stirred for 2 hours. After the reaction mixture was cleared, 4-[3-(3-aminophenyl)phenyl]-2-(3-pyridylmethyl)- 3-oxo-3,4-dihydropyrido[2,3-b]pyrazine (1.0 g) was added thereto and the mixture was stirred under reflux for 2 hours. The reaction mixture was washed with sodium bicarbonate solution and water, dried over magnesium sulfate and concentrated. Crude residue was chromatographed on silica gel (70 g, chloroform-methanol 100:1 as eluent) to give 4-[3-[3-[2-(3-pyridyl)thiazol-4-ylcarbonylamino]phenyl]phenyl]-2-(3-pyridylmethyl)-3-oxo-3,4-dihydropyrido[2,3-b]pyrazine as colorless crystals (0.48 g).

mp: 199–200þC.

NMR (DMSO-d$_6$, δ): 4.28 (2H, s), 7.38 (3H, m), 7.50 (2H, m), 7.60 (1H, dd, J=8, 5Hz), 7.70 (2H, m), 7.80 (1H, m), 7.85 (1H, m), 7.95 (1H, m), 8.20 (2H, m), 8.41 (1H, m), 8.48 (1H, m), 8.50 (1H, m), 8.58 (2H, m), 8.73 (1H, m), 9.40 (1H, s).

EXAMPLE 13

The mixture of 2-(bromomethyl)-4-[3-[2-(6-methoxy-5-bromo)naphthyl]phenyl]-3-oxo-3,4-dihydropyrido[2,3-b]pyrazine (4 g) and 1-acetylimidazole in N,N-dimethylformamide (40 ml) was stirred for 5 hours at 70þC. To the mixture was added saturated sodium carbonate (40 ml) and chloroform (40 ml). The mixture was stirred for 30 minutes. The mixture was extracted by chloroform (2×40 ml). The organic layer was evaporated in vacuo. The crude product was purified by chromatography to obtain 2-(1-imidazolylmethyl)-4-[3-[(6-methoxy-5-bromo)-2-naphthyl]phenyl]-3-oxo-3,4-dihydropyrido[2,3-b]pyrazine (1.7 g).

mp: 141–145þC.

NMR (CDCl$_3$, δ): 4.03 (3H, s), 5.43 (2H, s), 7.12 (1H, m), 7.17 (1H, m), 7.30 (2H, m), 7.35 (1H, dd, J=8, 5Hz), 7.61 (1H, m), 7.70 (1H, d, J=8Hz), 7.75 (1H, m), 7.85 (3H, m), 8.01 (1H, s), 8.21 (1H, d, J=8Hz), 8.28 (1H, d, J=8Hz), 8.50 (1H, m)

MASS (m/z): 538 (M+1), 540.

What is claimed is:

1. A compound of the formula:

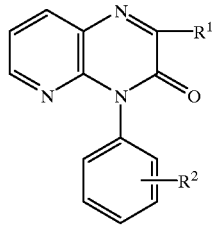

wherein

R$^1$ is pyridyl(lower)alkyl, N-oxidopyridyl(lower)alkyl or imidazolyl(lower)alkyl, R$^2$ is aminophenyl, [protected amino]phenyl, [[[halophenyl](lower)alkenoyl]amino]phenyl, [[pyridyl(lower)alkenoyl]amino]phenyl, [[[N-oxidopyridyl](lower)alkenoyl]amino]phenyl, [[[protected aminopyridyl](lower)alkenoyl]amino]phenyl, [thiazolylcarbonylamino]phenyl which may have pyridyl on thiazolyl, naphthyl having lower alkoxy and halogen, [dihalophenyl](lower)alkenyl, [N-oxidopyridyl](lower)alkenyl, [aminopyridyl](lower)alkenyl, [protected aminopyridyl](lower)alkenyl, [carboxypyridyl](lower)alkenyl, [protected carboxypyridyl](lower)alkenyl, [[pyridyl(lower)alkenyl]pyridyl](lower)alkenyl, [[carboxy(lower)alkenyl]pyridyl](lower)alkenyl, [[protected carboxy(lower)alkenyl]pyridyl](lower)alkenyl, [pyridyl(lower)alkenyl]pyridyl, lower alkylbenzothiazolyl or [halopyridylcarbonyl]amino, with proviso that when R$^2$ is [[4-pyridyl(lower)alkenoyl]amino]phenyl, aminophenyl, [lower alkanoylamino]phenyl or [dihalophenyl](lower)alkenyl, then R$^1$ is N-oxidopyridyl(lower)alkyl or imidazolyl(lower)alkyl, and a pharmaceutically acceptable salt thereof.

2. The compound of claim 1, wherein

R$^1$ is pridyl(lower)alkyl, N-oxidopyridyl(lower)alkyl or imidazolyl(lower)alkyl, R$^2$ is aminophenyl,
[lower alkanoylamino]phenyl,
[[[halophenyl](lower)alkenoyl]amino]phenyl,
[[pyridyl(lower)alkenoyl]amino]phenyl,
[[[N-oxidopyridyl](lower)alkenoyl]amino]phenyl,
[[[acylaminopyridyl](lower)alkenoyl]amino]phenyl,
[[pyridylthiazolyl]carbonylamino]phenyl,
naphthyl having lower alkoxy and halogen,
[dihalophenyl](lower)alkenyl,
[N-oxidopyridyl](lower)alkenyl,
[aminopyridyl](lower)alkenyl,
[[acylamino]pyridyl](lower)alkenyl,

[carboxypyridyl](lower)alkenyl,
[esterified carboxypyridyl](lower)alkenyl,
[[pyridyl(lower)alkenyl]pyridyl](lower)alkenyl,
[[carboxy(lower)alkenyl]pyridyl](lower)alkenyl,
[[esterified carboxy(lower)alkenyl]pyridyl](lower)alkenyl,
[pyridyl(lower)alkenyl]pyridyl,
lower alkylbenzothiazolyl or
halopyridylcarbonylamino, with the proviso that when $R^2$ is [[4-pyridyl(lower)alkenoyl]amino]phenyl, aminophenyl, [lower alkanoylamino]phenyl or [dihalophenyl](lower)alkenyl, then $R^1$ is N-oxidopyridyl(lower)alkyl or imidazolyl(lower)alkyl.

3. The compound of claim 2, wherein $R^1$ is pyridyl(lower)alkyl, and $R^2$ is [[2-pyridyl(lower)alkenoyl]amino]phenyl, [[3-pyridyl(lower)alkenoyl]amino]phenyl, [[pyridylthiazolyl]carbonylamino]phenyl, [aminopyridyl](lower)alkenyl, [[lower alkanoylamino]pyridyl](lower)alkenyl, [[trihalo(lower)alkanoylaino]pyridyl](lower)alkenyl, [lower alkoxycarbonylpyridyl](lower)alkenyl, [[pyridyl(lower)alkenyl]pyridyl](lower)alkenyl or lower alkylbenzothiazolyl.

4. The compound of claim 2, wherein $R^1$ is imidazolyl(lower)alkyl, and $R^2$ is naphthyl having lower alkoxy and halogen.

5. A process for preparing a compound of the formula:

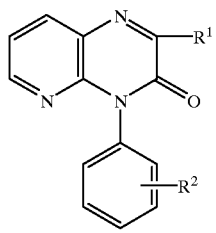

wherein $R^1$ and $R^2$ are each as defined in claim 1, or a salt thereof, which comprises (1) reacting a compound of the formula:

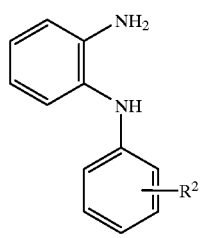

wherein $R^2$ is as defined above,
or a salt thereof with a compound of the formula:

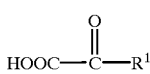

wherein $R^1$ is as defined above,
or a salt thereof to give a compound of the formula:

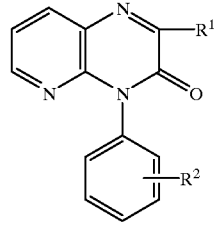

wherein $R^1$ and $R^2$ are each as defined above,
or a salt thereof, or (2) subjecting a compound of the formula:

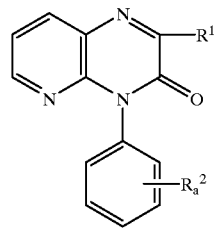

wherein $R^1$ is as defined above, and
$R_a^2$ is [aminopyridyl](lower)alkenyl, or its reactive derivative at the amino group, or a salt thereof to acylation reaction to give a compound of the formula:

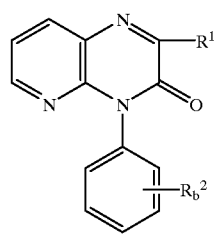

wherein $R^1$ is as defined above and
$R_b^2$ is [acylaminopyridyl](lower)alkenyl, or a salt thereof, or (3) subjecting a compound of the formula:

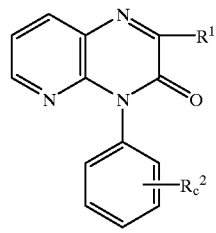

wherein
$R^1$ is as defined above,
$R_c^2$ is [lower alkanoylamino]phenyl, [[[halophenyl](lower)alkenoyl]amino]phenyl, [[pyridyl(lower)alkenoyl]amino]phenyl, [[[N-oxidopyridyl](lower)alkenoyl]amino]phenyl, [[[protected aminopyridyl](lower)alkenoyl]amino]phenyl,

[thiazolylcarbonylamino]phenyl which may have pyridyl or [acylaminopyridyl](lower)alkenyl,
or a salt thereof to deacylation to give a compound of the formula:

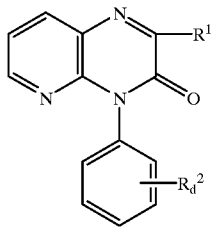

wherein
R¹ is as defined above, and
$R_d^2$ is aminophenyl or [aminopyridyl](lower)alkenyl,
or a salt thereof, or
(4) reacting a compound of the formula:

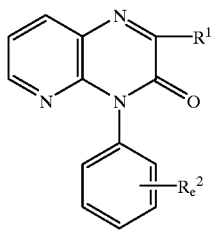

wherein
R¹ is as defined above, and
$R_e^2$ is aminophenyl,
or its reactive derivative at the amino group, or a salt thereof with a compound of the formula:

R³—OH wherein
R³ is lower alkanoyl, [halophenyl](lower)alkenoyl, pyridyl(lower)alkenoyl, [N-oxidopyridyl](lower)alkenoyl, [protected aminopyridyl](lower)alkenoyl or thiazolylcarbonyl which may have pyridyl,
or its reactive derivative at the carboxy group,
or a salt thereof to give a compound of the formula:

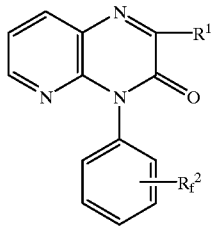

wherein
R¹ is as defined above, and
$R_f^2$ is [lower alkanoylamino]phenyl, [[[halophenyl] (lower)alkenoyl]amino]phenyl, [[pyridyl(lower) alkenoyl]amino]phenyl, [[[N-oxidopyridyl](lower) alkenoyl]amino]phenyl, [[[protected aminopyridyl] (lower)alkenoyl]amino]phenyl or [thiazolylcarbonylamino]phenyl which may have pyridyl,
or a salt thereof, (5) subjecting a compound of the formula:

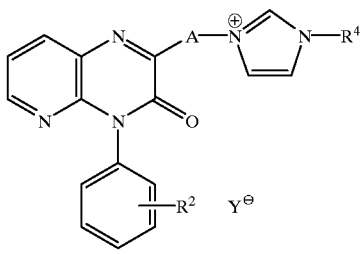

wherein
R² is as defined above,
R⁵ is N-protective group,
A is lower alkylene, and
Y⁻ is halide,
or a salt thereof to elimination of N-protective group to give a compound of the formula:

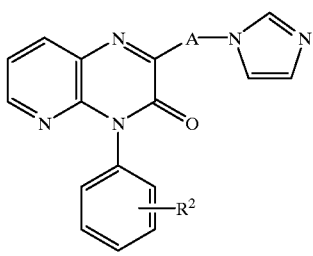

wherein R² and A are each as defined above, or a salt thereof.

6. A pharmaceutical composition which comprises, as an active ingredient, a compound of claim 1 or a pharmaceutically acceptable salt thereof in admixture with pharmaceutically acceptable carriers.

7. A method for the prophylactic or therapeutic treatment of phosphodiesterase IV (PDE-IV) and tumor necrosis factor (TNF) mediated diseases which comprises administering a compound of claim 1 or a pharmaceutically acceptable salts thereof to human or animals.

8. A process for preparing a pharmaceutical composition which comprises admixing a compound of claim 1 or a pharmaceutically acceptable salt thereof with a pharmaceutically acceptable carrier.

9. The compound of claim 2, wherein

[[[acylaminopyridyl](lower)alkenoyl]amino]phenyl is [[[[lower alkanoylamino]pyridyl](lower)alkenoyl] amino]phenyl);

[[acylamino]pyridyl](lower)alkenyl is [[lower alkanoylamino]pyridyl](lower)alkenyl or [[mono (or di or tri)halo (lower)alkanoylamino]pyridyl](lower) alkenyl;

[esterified carboxypyridyl](lower)alkenyl is [lower alkoxycarbonylpyridyl](lower)alkenyl; and

[[esterified carboxy(lower)alkenyl]pyridyl](lower) alkenyl is [[lower alkoxycarbonyl(lower)alkenyl] pyridyl](lower)alkenyl.

* * * * *